(12) United States Patent
Xu et al.

(10) Patent No.: US 7,199,277 B2
(45) Date of Patent: Apr. 3, 2007

(54) PRETREATING A CATALYST CONTAINING MOLECULAR SIEVE AND ACTIVE METAL OXIDE

(75) Inventors: Teng Xu, Houston, TX (US); Nicolas P. Coute, Houston, TX (US); Kenneth R. Clem, Humble, TX (US); Doron Levin, Annandale, NJ (US); James C. Vartuli, Schwenksville, PA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 169 days.

(21) Appl. No.: 10/883,438

(22) Filed: Jul. 1, 2004

(65) Prior Publication Data

US 2006/0004240 A1    Jan. 5, 2006

(51) Int. Cl.
C07C 1/00 (2006.01)
B01J 27/182 (2006.01)
B01J 21/00 (2006.01)

(52) U.S. Cl. ............... 585/640; 585/639; 502/208; 502/214; 502/240; 502/263; 502/303; 502/349

(58) Field of Classification Search ......... 585/639, 585/640; 502/208, 214, 240, 263, 303, 349
See application file for complete search history.

(56) References Cited

U.S. PATENT DOCUMENTS

| | | |
|---|---|---|
| 2,768,127 A | 10/1956 | Kimberlin, Jr. et al. |
| 2,949,493 A | 8/1960 | Happel et al. |
| 3,258,455 A | 6/1966 | Natta et al. |
| 3,305,538 A | 2/1967 | Natta et al. |
| 3,364,190 A | 1/1968 | Emrick |
| 3,645,992 A | 2/1972 | Elston |
| 3,785,782 A | 1/1974 | Cartmell |
| 4,035,284 A | 7/1977 | Gross et al. |
| 4,044,061 A | 8/1977 | Chang et al. |
| 4,060,568 A | 11/1977 | Rodewald |
| 4,062,905 A | 12/1977 | Chang et al. |
| 4,068,136 A | 1/1978 | Minami |
| 4,076,698 A | 2/1978 | Anderson et al. |
| 4,076,796 A | 2/1978 | Reh et al. |
| 4,079,095 A | 3/1978 | Givens et al. |
| 4,079,096 A | 3/1978 | Givens et al. |
| 4,086,186 A | 4/1978 | Rubin et al. |
| 4,090,981 A | 5/1978 | Rodewald |
| 4,100,219 A | 7/1978 | Rodewald |
| 4,134,926 A | 1/1979 | Tsao et al. |
| 4,145,315 A | 3/1979 | Rodewald |
| 4,156,698 A | 5/1979 | Dwyer et al. |
| 4,229,608 A | 10/1980 | Chen et al. |
| 4,231,899 A | 11/1980 | Chen et al. |
| 4,243,691 A | 1/1981 | Mohlenkamp, Jr et al. |
| 4,302,565 A | 11/1981 | Goeke et al. |
| 4,302,620 A | 11/1981 | Chu |
| 4,302,621 A | 11/1981 | Chu |
| 4,310,440 A | 1/1982 | Wilson et al. |
| 4,372,878 A | 2/1983 | Wunder et al. |
| 4,387,263 A | 6/1983 | Vogt et al. |
| 4,402,867 A | 9/1983 | Rodewald |
| 4,404,095 A | 9/1983 | Haddad et al. |
| 4,419,221 A | 12/1983 | Castagnos, Jr. et al. |
| 4,440,871 A | 4/1984 | Lok et al. |
| 4,465,889 A | 8/1984 | Anthony et al. |
| 4,477,583 A | 10/1984 | Rodewald |
| 4,481,376 A | 11/1984 | Wunder et al. |
| 4,499,314 A | 2/1985 | Seddon et al. |
| 4,499,327 A | 2/1985 | Kaiser |
| 4,500,651 A | 2/1985 | Lok et al. |
| 4,524,234 A | 6/1985 | Kaiser |
| 4,550,217 A | 10/1985 | Graziani et al. |
| 4,551,236 A | 11/1985 | Lok et al. |
| 4,552,645 A | 11/1985 | Gartside et al. |
| 4,554,143 A | 11/1985 | Messina et al. |
| 4,554,260 A | 11/1985 | Peters et al. |
| 4,567,029 A | 1/1986 | Wilson et al. |
| 4,579,999 A | 4/1986 | Gould et al. |
| 4,594,332 A | 6/1986 | Hoelderich et al. |
| 4,605,492 A | 8/1986 | Lok et al. |
| 4,638,106 A | 1/1987 | Pieters et al. |
| 4,659,685 A | 4/1987 | Coleman, III et al. |
| 4,664,888 A | 5/1987 | Castagnos, Jr. |
| 4,677,242 A | 6/1987 | Kaiser |
| 4,677,243 A | 6/1987 | Kaiser |
| 4,683,334 A | 7/1987 | Bergna et al. |
| 4,752,651 A | 6/1988 | Kaiser |
| 4,780,196 A | 10/1988 | Alagy et al. |
| 4,814,067 A | 3/1989 | Gartside et al. |
| 4,861,743 A | 8/1989 | Flank et al. |

(Continued)

FOREIGN PATENT DOCUMENTS

DE            270526 A1    8/1989

(Continued)

OTHER PUBLICATIONS

Kang et al., "Effects of Decrease in Number of Acid Sites Located on the External Surface of Ni-SAPO-34 Crystalline Catalyst by the Mechanochemical Method," Catalysis Letter, vol. 53, pp. 171-176 (1998).*

(Continued)

*Primary Examiner*—Glen Caldarola
*Assistant Examiner*—In Suk Bullock

(57) ABSTRACT

This invention relates to processes for converting oxygenates to olefins that include a step of pretreating catalyst, which comprises molecular sieve and one or more active metal oxides of one or more metals, with a hydrocarbon composition to provide an integrated hydrocarbon co-catalyst within the molecular sieve. The combination of molecular sieve and hydrocarbon co-catalyst converts oxygenate to an olefin product with high selectivity to light olefins (i.e., ethylene or propylene, or mixture thereof).

67 Claims, No Drawings

U.S. PATENT DOCUMENTS

| | | |
|---|---|---|
| 4,861,938 A | 8/1989 | Lewis et al. |
| 4,873,390 A | 10/1989 | Lewis et al. |
| 4,929,780 A | 5/1990 | Wright et al. |
| 4,943,424 A | 7/1990 | Miller |
| 5,071,450 A | 12/1991 | Cabrera et al. |
| 5,095,163 A | 3/1992 | Barger |
| 5,096,684 A | 3/1992 | Guth et al. |
| 5,098,880 A | 3/1992 | Gaffney et al. |
| 5,126,308 A | 6/1992 | Barger et al. |
| 5,157,181 A | 10/1992 | Stine et al. |
| 5,176,817 A | 1/1993 | Skeels et al. |
| 5,191,141 A | 3/1993 | Barger et al. |
| 5,233,117 A | 8/1993 | Barger et al. |
| 5,234,875 A | 8/1993 | Han et al. |
| 5,250,484 A | 10/1993 | Beck et al. |
| 5,278,345 A | 1/1994 | Janssen et al. |
| 5,279,810 A | 1/1994 | Calabro |
| 5,324,493 A | 6/1994 | Mueller et al. |
| 5,343,830 A | 9/1994 | Alexander et al. |
| 5,349,113 A | 9/1994 | Chang et al. |
| 5,349,114 A | 9/1994 | Lago et al. |
| 5,365,003 A | 11/1994 | Chang et al. |
| 5,367,100 A | 11/1994 | Gongwei et al. |
| 5,417,949 A | 5/1995 | McWilliams et al. |
| 5,455,213 A | 10/1995 | Chang et al. |
| 5,475,182 A | 12/1995 | Janssen |
| 5,476,823 A | 12/1995 | Beck et al. |
| 5,541,146 A | 7/1996 | Chang et al. |
| 5,663,471 A | 9/1997 | Kvisle et al. |
| 5,689,025 A | 11/1997 | Abichandani et al. |
| 5,714,662 A | 2/1998 | Vora et al. |
| 5,714,663 A | 2/1998 | Serrand et al. |
| 5,744,673 A | 4/1998 | Skeels et al. |
| 5,744,680 A | 4/1998 | Mulvaney, III et al. |
| 5,892,079 A | 4/1999 | Wilson, Jr. |
| 5,904,880 A | 5/1999 | Sun |
| 5,907,076 A | 5/1999 | Ou et al. |
| 5,912,393 A | 6/1999 | Barger et al. |
| 5,925,586 A | 7/1999 | Sun |
| 5,925,800 A | 7/1999 | Sun et al. |
| 5,927,063 A | 7/1999 | Jandes et al. |
| 5,932,512 A | 8/1999 | Sun |
| 5,952,538 A | 9/1999 | Vaughn et al. |
| 5,960,643 A | 10/1999 | Kuechler et al. |
| 5,962,762 A | 10/1999 | Sun et al. |
| 5,972,203 A | 10/1999 | Smith et al. |
| 6,001,328 A | 12/1999 | Lillerod et al. |
| 6,004,898 A | 12/1999 | Sun |
| 6,005,155 A | 12/1999 | Sun |
| 6,023,005 A | 2/2000 | Lattner et al. |
| 6,034,020 A | 3/2000 | Drake et al. |
| 6,040,257 A | 3/2000 | Drake et al. |
| 6,040,264 A | 3/2000 | Sun et al. |
| 6,046,371 A | 4/2000 | Wu et al. |
| 6,046,372 A | 4/2000 | Brown et al. |
| 6,046,373 A | 4/2000 | Sun |
| 6,048,816 A | 4/2000 | Brown et al. |
| 6,051,745 A | 4/2000 | Wu et al. |
| 6,051,746 A | 4/2000 | Sun et al. |
| 6,057,261 A | 5/2000 | Sun |
| 6,121,503 A | 9/2000 | Janssen et al. |
| 6,121,504 A | 9/2000 | Kuechler et al. |
| 6,137,022 A | 10/2000 | Kuechler et al. |
| 6,166,282 A | 12/2000 | Miller |
| 6,174,339 B1 | 1/2001 | Varady |
| 6,180,828 B1 | 1/2001 | Hidaka et al. |
| 6,225,254 B1 | 5/2001 | Janssen et al. |
| 6,316,683 B1 | 11/2001 | Janssen et al. |
| 6,436,869 B1 | 8/2002 | Searle et al. |
| 6,437,208 B1 | 8/2002 | Kuechler et al. |
| 6,657,022 B2 * | 12/2003 | Williams et al. ............... 526/72 |
| 6,844,291 B2 * | 1/2005 | Levin et al. ................. 502/214 |
| 6,906,232 B2 * | 6/2005 | Levin et al. ................. 585/638 |
| 6,995,111 B2 * | 2/2006 | Levin et al. ................. 502/214 |
| 2003/0176733 A1 | 9/2003 | Kunhle et al. |
| 2003/0176753 A1 | 9/2003 | Levin et al. |

FOREIGN PATENT DOCUMENTS

| | | |
|---|---|---|
| EP | 096 996 | 12/1983 |
| EP | 0 312 981 | 4/1989 |
| WO | WO88/01254 | 2/1988 |
| WO | WO93/17788 | 9/1993 |
| WO | WO93/24431 | 12/1993 |
| WO | WO96/28408 | 9/1996 |
| WO | WO98/29363 | 7/1998 |
| WO | WO 98/29370 * | 7/1998 |
| WO | WO 01/62382 A2 * | 8/2001 |
| WO | WO 01/64340 A1 * | 9/2001 |

OTHER PUBLICATIONS

Blackwell et al., *Solid-State MNR of Silicoaluminophosphate Molecular Sieves and Aluminophosphate Materials*, J. Phys. Chem., vol. 92, pp. 3965-3970 (1988).

Zenz et al., *Riser Reactor*, Fluidization and Fluid-Particle Systems, Reinhold Publishing Corp. NY, pp. 48-59 (1960).

Schulz et al., "Kinetic regimes of zeolite deactivation and reanimation," Applied Catalysis A: General 132 (1995), pp. 29-40.

Prakash, A.M., "Synthesis of SAPO-34: High Silicon Incorporation in the Presence of Morpholine as Template," J.Chem. Soc., Faraday Trans., 1994, 90(15), pp. 2291-2296.

Lysenko et al., "Passivation of Vanadium and Nickel on Cracking Catalysts," Neftekhimiya 28, No. 3, pp. 356-358 (1988).

Chen et al., "Understanding the Bronsted Acidity of SAPO-5, SAPO-17, SAPO-18 and SAPO-34 and their Catalytic Performance for Methanol Conversion to Hydrocarbons," Studies in Surface Sciences and Catalysts, Proceedings of the Tenth International Catalysis Society, vol. 84, pp. 1731-1738 (1994).

Schulz et al., "Deactivation and thermal regeneration of zeolite HZSM-5 for methanol conversion at low temperature (260-290° C.)", Microporous and Mesoporous Materials 29 (1999), pp. 205-218.

De Chen et al., "The Role of Coke Deposition in the Conversion of Methanol to Olefins over SAPO-34," Stud. Surf. Sci. Catal., 111 (Catalyst Deactivation 1997), pp. 159-166.

Hutchings et al., "Methanol conversion to hydrocarbons over zeolite H-ZSM-5: Comments on the formation of $C_4$ hydrocarbons at low reaction temperatures," Applied Catalysis A: General, 106 (1993), pp. 115-123.

Groenvold et al., "Conversion of methanol to lower alkenes on molecular sieve type catalysts," Stud. Surf. Sci., Catal., 81 (Natural Gas Conversion 11), pp. 399-404 (1994).

* cited by examiner

PRETREATING A CATALYST CONTAINING MOLECULAR SIEVE AND ACTIVE METAL OXIDE

FIELD OF THE INVENTION

This invention relates to processes for converting oxygenates to olefins. In particular, this invention relates to processes for converting oxygenates to olefins that include a step of pretreating catalyst, which comprises molecular sieve and one or more active metal oxides of one or more metals, with a hydrocarbon composition to provide an integrated hydrocarbon co-catalyst within the molecular sieve.

BACKGROUND OF THE INVENTION

Methanol is used as a feed stock for a variety of chemical manufacturing processes. One process that is more recently being developed is the conversion of methanol to olefin products, particularly products containing the olefins ethylene and propylene. The olefins produced from the methanol conversion process are of suitable quality to be used in polymer manufacturing processes. Of a commercial concern in the methanol conversion process, however, is whether sufficient quantities of light olefins (i.e., ethylene and propylene) can be produced. Another concern is whether an appropriate catalyst can be supplied at sufficient quantities to meet the rigors of commercial scale processing.

Conventional molecular sieves used in converting oxygenates to olefins are zeolites and various metalloaluminophosphates. For example, U.S. Pat. No. 5,367,100 describes the use of the zeolite, ZSM-5, to convert methanol into olefin(s); U.S. Pat. No. 4,062,905 discusses the conversion of methanol and other oxygenates to ethylene and propylene using crystalline aluminosilicate zeolites, for example Zeolite T, ZK5, erionite and chabazite; U.S. Pat. No. 4,079,095 describes the use of ZSM-34 to convert methanol to hydrocarbon products such as ethylene and propylene; and U.S. Pat. No. 4,310,440 describes producing light olefin(s) from an alcohol using a crystalline aluminophosphate, often designated $AlPO_4$.

Some of the most useful molecular sieves for converting methanol to olefin(s) are silicoaluminophosphate molecular sieves. Silicoaluminophosphate (SAPO) molecular sieves contain a three-dimensional microporous crystalline framework structure of $[SiO_4]$, $[AlO_4]$ and $[PO_4]$ corner sharing tetrahedral units. SAPO synthesis is described in U.S. Pat. No. 4,440,871, which is herein fully incorporated by reference. SAPO molecular sieves are generally synthesized by the hydrothermal crystallization of a reaction mixture of silicon-, aluminum- and phosphorus-sources and at least one templating agent. Synthesis of a SAPO molecular sieve, its formulation into a SAPO catalyst, and its use in converting a hydrocarbon feedstock into olefin(s), particularly where the feedstock is methanol, are disclosed in U.S. Pat. Nos. 4,499,327, 4,677,242, 4,677,243, 4,873,390, 5,095,163, 5,714,662 and 6,166,282, all of which are herein fully incorporated by reference.

Typically, molecular sieves are formed into molecular sieve catalyst compositions (generally referred to as formulated catalysts) to improve their durability in commercial conversion processes. These formulated catalyst compositions are conventionally formed by combining molecular sieve, and one or more matrix materials, with a binder. The binder acts to hold the matrix material to the molecular sieve.

U.S. Pat. No. 4,465,889 describes a catalyst composition comprising a silicalite molecular sieve impregnated with a thorium, zirconium, or titanium active metal oxide for use in converting methanol, dimethyl ether, or a mixture thereof into a hydrocarbon product rich in iso-$C_4$ compounds.

U.S. Pat. No. 6,180,828 discusses the use of a modified molecular sieve to produce methylamines from methanol and ammonia, where for example, a silicoaluminophosphate molecular sieve is combined with one or more modifiers, such as a zirconium oxide, a titanium oxide, an yttrium oxide, montmorillonite or kaolinite.

U.S. Pat. No. 5,417,949 relates to a process for converting noxious nitrogen oxides in an oxygen containing effluent into nitrogen and water using a molecular sieve and a active metal oxide binder, where the preferred binder is titania and the molecular sieve is an aluminosilicate.

EP-A-312981 discloses a process for cracking vanadium-containing hydrocarbon feed streams using a catalyst composition comprising a physical mixture of a zeolite embedded in an inorganic refractory matrix material and at least one oxide of beryllium, magnesium, calcium, strontium, barium or lanthanum, preferably magnesium oxide, on a silica-containing support material.

Kang and Inui, "Effects of decrease in number of acid sites located on the external surface of Ni-SAPO-34 crystalline catalyst by the mechanochemical method," Catalysis Letters 53, pages 171–176 (1998) disclose that the shape selectivity can be enhanced and the coke formation mitigated in the conversion of methanol to ethylene over Ni-SAPO-34 by milling the catalyst with MgO, CaO, BaO or $Cs_2O$ on microspherical non-porous silica, with BaO being the most preferred.

International Publication No. WO 98/29370 discloses the conversion of oxygenates to olefins over a small pore non-zeolitic molecular sieve containing a metal selected from the group consisting of a lanthanide, an actinide, scandium, yttrium, a Group 4 metal, a Group 5 metal or combinations thereof.

U.S. Pat. No. 4,677,242 (Kaiser) describes the use of a silicoaluminophosphate (SAPO) molecular sieve catalyst for converting various oxygenates, such as methanol, to olefins. According to the patent, the SAPO catalyst is an extremely efficient catalyst for the conversion of oxygenates to light olefin products when the feed is converted in the presence of a diluent. The diluent used has an average kinetic diameter larger than the pores of the SAPO molecular sieve. The selected SAPO molecular sieves have pore sizes capable of absorbing oxygen (average kinetic diameter of about 3.36 angstroms), but with negligible adsorption of isobutane (average kinetic diameter of about 5.0 angstroms).

U.S. Pat. No. 6,046,372 (Brown et al.) discloses another method of converting methanol to light olefins. The method incorporates the use of medium pore zeolite molecular sieves, particularly medium pore ZSM type zeolites, in converting methanol and/or dimethyl ether to light olefin. Light olefin production is aided by the use of an aromatic compound as a co-feed. The aromatic compound has a critical diameter less than the pore size of the catalyst, and is capable of alkylation by the methanol and/or dimethyl ether. Ethylene product selectivity is believed to be derived from the back-cracking of ethyl-aromatic intermediates. The formation of the ethyl-aromatic intermediates is believed to be facilitated by a mechanism in which the aromatic compound effectively acts as a catalyst in the conversion of two molecules of methanol to one molecule of ethylene.

U.S. Pat. No. 6,051,746 (Sun et al.) also describes a method for increasing light olefin selectivity in the conversion of oxygenates using a small pore molecular sieve catalyst. The selectivity is increased by exposing a catalyst to a modifier before or during the conversion reaction. The modifier is a polynuclear aromatic having at least three interconnected ring structures, with each ring structure having at least 5 ring members. It is adsorbed onto the catalyst prior to or simultaneously with the introduction of feed.

U.S. Pat. No. 6,137,022 (Kuechler et al.) is to a process for increasing the selectivity of a reaction to convert oxygenates to olefins. The process involves contacting the oxygenate in a reaction zone containing 15 volume percent or less of a catalyst comprising SAPO molecular sieve, and maintaining conversion of the feedstock between 80% and 99% under conditions effective to convert 100% of the feedstock when the reaction zone contains at least 33 volume percent of the molecular sieve material. The process is considered to be beneficial in maximizing the production of ethylene and/or propylene, and to minimize the production of undesired products.

U.S. Pat. No. 6,225,254 (Janssen et al.) is directed to a method of maintaining acid catalyst sites of a SAPO molecular sieve catalyst. According to the patent, catalyst sites are lost when exposed to a moisture-containing environment. In order to maintain the catalyst sites, and thereby preserve catalyst activity, template-containing SAPO molecular sieves are heated in an oxygen depleted environment under conditions effective to provide an integrated catalyst life that is greater than that obtained in a non-oxygen depleted environment.

U.S. Pat. No. 6,436,869 (Searle et al.) is directed to a method of obtaining olefin product high in ethylene and/or propylene content, while reducing the amount of any one or more of $C_1$–$C_4$ paraffin by-products, and to reduce the amount of coke deposits on the catalyst during the reaction. The method is accomplished by providing a catalyst that comprises SAPO crystals, a binder comprising AlPO crystals, and nickel, cobalt and/or iron, wherein the catalyst does not contain significant amounts of amorphous binder, but rather contains crystalline AlPO.

U.S. Pat. No. 6,437,208 (Kuechler et al.) discloses a method for making olefin product from an oxygenate-containing feedstock. In the method, a SAPO molecular sieve catalyst is contacted with the oxygenate-containing feedstock in a reactor at an average catalyst feedstock exposure index of at least 1.0. The average catalyst feedstock exposure index is the total weight of oxygenate plus hydrocarbon fed to the reactor divided by the total weight of fresh and regenerated SAPO molecular sieve (i.e., excluding binder, inerts, etc., of the catalyst composition) sent to the reactor, both total weights measured over the same period of time. The method is shown to be effective in maintaining a high ethylene and propylene selectivity.

WO 01/62382 A2 (ExxonMobil Chemical Patents Inc.) discloses that selectivity to ethylene and propylene can be increased by pretreating a SAPO molecular sieve to form an integrated hydrocarbon co-catalyst within the framework of the molecular sieve prior to contacting with oxygenate feed. Acetone, methanol, propene, butene, pentene and hexene are given as examples of pretreatment compounds capable of forming an integrated hydrocarbon co-catalyst. The conditions for pretreatment include pretreating at a lower temperature relative to the reaction temperature. A preferred pretreatment vessel is an auxiliary fluidized bed reactor system associated with the oxygenate conversion reactor.

U.S. Patent Application, Publication No. US 2003/0176753 A1 (Levin et al.), discloses a catalyst composition comprising a molecular sieve and at least one oxide of a metal selected from Group 3 of the Periodic Table of Elements, the Lanthanide series of elements and the Actinide series of elements. The metal oxide has an uptake of carbon dioxide at 100° C. of at least 0.03, and typically at least 0.04, mg/m² of the metal oxide. The catalyst is useful in converting oxygenate compounds into one or more olefins, preferably ethylene and/or propylene.

U.S. Patent Application, Publication No. US 2003/0176752 A1 (Levin et al.), discloses another metal oxide catalyst composition useful in converting oxygenate compounds into one or more olefins, preferably ethylene and/or propylene. The catalyst composition comprises a molecular sieve and at least one oxide of a metal selected from Group 4 of the Periodic Table of Elements. The metal oxide has an uptake of carbon dioxide at 100° C. of at least 0.03, and typically at least 0.035, mg/m² of the metal oxide.

U.S. Patent Application, Publication No. US 2003/0176733 A1 (Xu et al.), discloses another type of metal oxide catalyst composition useful in converting oxygenate compounds into one or more olefins, preferably ethylene and/or propylene. The catalyst composition comprises a silicoaluminophosphate molecular sieve and a metal oxide which has a surface area greater than 20 m²/g, which has been calcined at temperature greater than 200° C. When saturated with acetone, and contacted with acetone for 1 hour at 25° C., the catalyst converts more than 80% of the acetone. The molecular sieve has an average pore size of less than 5 angstroms.

In spite of the recent technological advances in converting oxygenates to olefins, there remains a need to further increase the quantity of light olefins in the conversion product. In particular, there remains a need to increase product selectivity to ethylene and propylene, and particularly to ethylene. There also remains a need to reduce the amount of undesirable by-products in converting the oxygenates to olefins. Additionally, there remains a need to provide catalysts that have characteristics that enable the catalysts to endure the various rigors of commercial demands. Catalysts that have substantially increased catalyst lifetimes are also of value.

SUMMARY OF THE INVENTION

This invention provides processes for converting oxygenates to olefins that show enhanced selectivity to ethylene and/or propylene, as well as substantially increased catalyst lifetimes. The processes involve providing an oxygenate conversion catalyst that contains, inter alia, molecular sieve and one or more oxides of one or more metals, and pretreating the conversion catalyst with a hydrocarbon composition in a pretreatment zone.

In one aspect, there is provided a process for making an olefin product from an oxygenate feed. The process includes a step of providing a catalyst composition, wherein the catalyst comprises a metalloaluminophosphate molecular sieve having a porous framework and an active metal oxide. The catalyst composition is pretreated by contacting the catalyst composition (i.e., the molecular sieve in the catalyst composition) with a hydrocarbon in a pretreatment zone to form an integrated hydrocarbon co-catalyst within the porous framework of the molecular sieve. The pretreated catalyst composition is then contacted with an oxygenate in an oxygenate conversion zone to convert the oxygenate to olefin product.

The invention further provides a process for making an olefin product and polyolefin from an oxygenate feed. The process includes a step of providing a catalyst composition, wherein the catalyst comprises a metalloaluminophosphate molecular sieve having a porous framework and an active metal oxide. The catalyst composition is pretreated by contacting with a hydrocarbon in a pretreatment zone to form an integrated hydrocarbon co-catalyst within the porous framework of the molecular sieve. The pretreated catalyst composition is then contacted with an oxygenate in an oxygenate conversion zone to convert the oxygenate to olefin product, and at least one olefin in the olefin product is contacted with a polyolefin forming catalyst to form polyolefin.

The active metal oxide used in the catalyst of this invention, is desirably an active metal oxide of one or more metals selected from the group consisting of Group 2, Group 3 (including the Lanthanide series of metals, and the Actinide series of metals) and Group 4 metals of the Periodic Table. In one embodiment, the active metal oxide is an active metal oxide of one of the Group 2 metals and one or more of the Group 3 metals. In another embodiment, the active metal oxide is an active metal oxide of one of the Group 4 metals and one or more of the Group 2 or 3 metals.

In one embodiment of the invention, the active metal oxide has a carbon dioxide uptake at 100° C. of at least 0.03 mg/m$^2$ of the active metal oxide composition. Preferably, the active metal oxide has a carbon dioxide uptake at 100° C. of at least 0.035 mg/m$^2$ of the active metal oxide composition.

In another embodiment, the active metal oxide has a carbon dioxide uptake at 100° C. of less than 10 mg/m$^2$ of the active metal oxide. Preferably, the active metal oxide has a carbon dioxide uptake at 100° C. of less than 5 mg/m$^2$ of the active metal oxide.

In another embodiment, the active metal oxide has a surface area of at least 10 m$^2$/g. Preferably, the active metal oxide has a surface area of at least 15 m$^2$/g.

In yet another embodiment of the invention, the active metal oxide comprises at least one active metal oxide selected from the group consisting of zirconium oxide, magnesium oxide, calcium oxide, barium oxide, lanthanum oxide, yttrium oxide, scandium oxide and cerium oxide.

Desirably, the metalloaluminophosphate molecular sieve is silicoaluminophosphate molecular sieve. Preferably, the metalloaluminophosphate molecular sieve is comprised of one or a combination of molecular sieves selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AlPO-5, AlPO-11, AlPO-18, AlPO-31, AlPO-34, AlPO-36, AlPO-37, AlPO-46, and metal containing molecular sieves thereof.

Optionally, the catalyst composition comprises an alumina binder. The catalyst composition also optionally comprises a clay.

Preferably, the hydrocarbon contacting the molecular sieve in the pretreatment zone has a kinetic diameter less than the average pore opening of the molecular sieve. In one embodiment, the hydrocarbon contacting the molecular sieve in the pretreatment zone comprises an alcohol, olefin, aldehyde, ketone, ether, or any combination thereof. In another embodiment, the hydrocarbon contacting the molecular sieve in the pretreatment zone comprises methanol, ethanol or any combination thereof. In another, the hydrocarbon contacting the molecular sieve in the pretreatment zone comprises butene, pentene, hexene, heptene or any combination thereof. In yet another, the hydrocarbon contacting the molecular sieve in the pretreatment zone comprises acetaldehyde, propionaldehyde, butyraldehyde or any combination thereof. In still another, the hydrocarbon contacting the molecular sieve in the pretreatment zone comprises acetone, butanone, pentanone or any combination thereof. In another, the hydrocarbon contacting the molecular sieve in the pretreatment zone comprises dimethyl ether, methyl ethyl ether, diethyl ether, methyl propyl ether, ethyl propyl ether, dipropyl ether, methyl butyl ether, ethyl butyl ether, propyl butyl ether, dibutyl ether or any combination thereof.

The pretreatment zone can be operated at varying degrees of temperature. In one embodiment, the pretreatment zone is at a temperature higher than that of the oxygenate conversion zone. Preferably, the pretreatment zone is at a temperature of at least 10° C. higher, more preferably at least 20° C. higher, and most preferably at least 50° C. higher than that of the oxygenate conversion zone.

DETAILED DESCRIPTION OF THE INVENTION

I. Pretreatment of Molecular Sieve with Hydrocarbon

This invention is directed to processes for making olefin product from an oxygenate feed. The processes include a step of pretreating a fresh or regenerated molecular sieve catalyst with a hydrocarbon composition. The hydrocarbon in the composition forms a hydrocarbon co-catalyst within the pore structure of the molecular sieve. This combination of molecular sieve and hydrocarbon co-catalyst converts oxygenate to an olefin product with high selectivity to light olefins (i.e., ethylene or propylene, or mixture thereof).

The molecular sieve catalyst of the invention contains a metalloaluminophosphate molecular sieve that further acts to convert the oxygenate to an olefin product, with high selectivity to light olefins. In addition, the catalyst contains one or more active metal oxides of one or more metals. This active metal oxide composition substantially increases the lifetime of the catalyst, meaning that the catalyst can be used for longer periods of time during the reaction process. The invention, therefore, provides processes for converting oxygenates to olefins that are very high in selectivity to ethylene and propylene products, and that operate at relatively long catalyst lifetimes.

II. Molecular Sieve and Metal Oxide Components

The catalysts of this invention comprise metalloaluminophosphate molecular sieve and one or more active metal oxides of one or more metals. The combination of metalloaluminophosphate molecular sieve and active metal oxide provides a catalyst that has a longer catalyst lifetime in oxygenate conversion reactions and produces additional ethylene and propylene products with lower amounts of undesirable ethane and propane by-products.

A. Metalloaluminophosphate Molecular Sieves

Metalloaluminophosphate molecular sieves have a molecular framework that include [AlO$_4$] and [PO$_4$] tetrahedral units, such as metal containing aluminophosphates (AlPO). In one embodiment, the metalloaluminophosphate molecular sieves include [AlO$_4$], [PO$_4$] and [SiO$_4$] tetrahedral units, such as silicoaluminophosphates (SAPO).

Various silicon, aluminum, and phosphorus based molecular sieves and metal-containing derivatives thereof have been described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0 159 624 (ELAPSO where El is As, Be, B, Cr, Co, Ga, Ge, Fe, Li, Mg, Mn, Ti or Zn), U.S. Pat. No. 4,554,143 (FeAPO), U.S. Pat.

Nos. 4,822,478, 4,683,217, 4,744,885 (FeAPSO), EP-A-0 158 975 and U.S. Pat. No. 4,935,216 (ZnAPSO, EP-A-0 161 489 (CoAPSO), EP-A-0 158 976 (ELAPO, where EL is Co, Fe, Mg, Mn, Ti or Zn), U.S. Pat. No. 4,310,440 (AlPO4), EP-A-0 158 350 (SENAPSO), U.S. Pat. No. 4,973,460 (LiAPSO), U.S. Pat. No. 4,789,535 (LiAPO), U.S. Pat. No. 4,992,250 (GeAPSO), U.S. Pat. No. 4,888,167 (GeAPO), U.S. Pat. No. 5,057,295 (BAPSO), U.S. Pat. No. 4,738,837 (CrAPSO), U.S. Pat. Nos. 4,759,919, and 4,851,106 (CrAPO), U.S. Pat. Nos. 4,758,419, 4,882,038, 5,434,326 and 5,478,787 (MgAPSO), U.S. Pat. No. 4,554,143 (FeAPO), U.S. Pat. No. 4,894,213 (AsAPSO), U.S. Pat. No. 4,913,888 (AsAPO), U.S. Pat. Nos. 4,686,092, 4,846,956 and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617 and 4,880,520 (TiAPSO), U.S. Pat. Nos. 4,500, 651, 4,551,236 and 4,605,492 (TiAPO), U.S. Pat. Nos. 4,824,554, 4,744,970 (CoAPSO), U.S. Pat. No. 4,735,806 (GaAPSO) EP-A-0 293 937 (QAPSO, where Q is framework oxide unit [$QO_2$]), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,241,093, 5,493,066 and 5,675,050, all of which are herein fully incorporated by reference. Other molecular sieves include those described in R. Szostak, Handbook of Molecular Sieves, Van Nostrand Reinhold, New York, N.Y. (1992), which is herein fully incorporated by reference.

The more preferred molecular sieves are SAPO molecular sieves, and metal-substituted SAPO molecular sieves. Suitable metal substituents are alkali metals of Group IA of the Periodic Table of Elements, an alkaline earth metals of Group IIA of the Periodic Table of Elements, a rare earth metals of Group IIIB, including the Lanthanides: lanthanum, cerium, praseodymium, neodymium, samarium, europium, gadolinium, terbium, dysprosium, holmium, erbium, thulium, ytterbium and lutetium; and scandium or yttrium of the Periodic Table of Elements, transition metals of Groups IVB, VB, VIIB, VIIB, VIIIB, and EB of the Periodic Table of Elements and mixtures of any of these metal species. In one embodiment, the metal is selected from the group consisting of Co, Cr, Cu, Fe, Ga, Ge, Mg, Mn, Ni, Sn, Ti, Zn and Zr, and mixtures thereof. The metal atoms may be inserted into the framework of a molecular sieve through a tetrahedral unit, such as [$MeO_2$], and carry a net charge depending on the valence state of the metal substituent. For example, in one embodiment, when the metal substituent has a valence state of +2, +3, +4, +5, or +6, the net charge of the tetrahedral unit is between −2 and +2.

In one embodiment, the metalloaluminophosphate molecular sieve is represented, on an anhydrous basis, by the formula:

$$mR:(M_xAl_yP_z)O_2$$

wherein R represents at least one templating agent, preferably an organic templating agent; m is the number of moles of R per mole of $(M_xAl_yP_z)O_2$ and m has a value from 0 to 1, preferably 0 to 0.5, and most preferably from 0 to 0.3; x, y, and z represent the mole fraction of Al, P and M as tetrahedral oxides, where M is a metal selected from the group consisting of Group IA, IIA, IB, IIIB, IVB, VB, VIIB, VIIB, VIIIB and Lanthanide's of the Periodic Table of Elements. Preferably M is one or more metals selected from the group consisting of Si, Co, Cr, Cu, Fe, Ga, Ge, Mg, Mn, Ni, Sn, Ti, Zn and Zr. In an embodiment, m is greater than or equal to 0.2, and x, y and z are greater than or equal to 0.01. In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

In one embodiment of the invention, the metalloaluminophosphate molecular sieves contain silicon and aluminum. Desirably, the metalloaluminophosphate molecular sieves of this invention contain Si and Al, at a Si/Al ratio of not greater than about 0.5, preferably not greater than about 0.3, more preferably not greater than about 0.2, still more preferably not greater than about 0.15, and most preferably not greater than about 0.1. In another embodiment, the Si/Al ratio is sufficiently high to allow for increased catalytic activity of the molecular sieve. Preferably, the metalloaluminophosphate molecular sieves contain Si and Al at a ratio of at least about 0.005, more preferably at least about 0.01 and most preferably at least about 0.02.

Non-limiting examples of SAPO and AlPO molecular sieves useful herein include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AlPO-5, AlPO-11, AlPO-18, AlPO-31, AlPO-34, AlPO-36, AlPO-37, AlPO-46, and metal containing molecular sieves thereof. Of these, particularly useful molecular sieves are one or a combination of SAPO-18, SAPO-34, SAPO-35, SAPO-44, SAPO-56, AlPO-18, AlPO-34 and metal containing derivatives thereof, such as one or a combination of SAPO-18, SAPO-34, AlPO-34, AlPO-18, and metal containing derivatives thereof, and especially one or a combination of SAPO-34, AlPO-18, and metal containing derivatives thereof.

In an embodiment, the molecular sieve is an intergrowth material having two or more distinct crystalline phases within one molecular sieve composition. In particular, intergrowth molecular sieves are described in U.S. Patent Application Publication No. 2002-0165089 and International Publication No. WO 98/15496, published Apr. 16, 1998, both of which are herein fully incorporated by reference. For example, SAPO-18, AlPO-18 and RUW-18 have an AEI framework-type, and SAPO-34 has a CHA framework-type. Thus, the molecular sieve used herein may comprise at least one intergrowth phase of AEI and CHA framework-types, especially where the ratio of CHA framework-type to AEI framework-type, as determined by the DIFFaX method disclosed in U.S. Patent Application Publication No. 2002-0165089, is greater than 1:1.

Generally, molecular sieves (i.e., molecular sieve crystals) are synthesized by the hydrothermal crystallization of one or more of a source of aluminum, a source of phosphorus, a source of silicon, water and a templating agent, such as a nitrogen containing organic compound. Typically, a combination of sources of silicon and aluminum, or silicon, aluminum and phosphorus, water and one or more templating agents, is placed in a sealed pressure vessel. The vessel is optionally lined with an inert plastic such as polytetrafluoroethylene, and heated under a crystallization pressure and temperature, until a crystalline material is formed, which can then be recovered by filtration, centrifugation and/or decanting.

Non-limiting examples of silicon sources include silicates, fumed silica, for example, Aerosil-200 available from Degussa Inc., New York, N.Y., and CAB-O-SIL M-5, organosilicon compounds such as tetraalkylorthosilicates, for example, tetramethylorthosilicate (TMOS) and tetraethylorthosilicate (TEOS), colloidal silicas or aqueous suspensions thereof, for example Ludox-HS-40 sol available from E.I. du Pont de Nemours, Wilmington, Del., silicic acid or any combination thereof.

Non-limiting examples of aluminum sources include aluminum alkoxides, for example aluminum isopropoxide, aluminum phosphate, aluminum hydroxide, sodium aluminate, pseudo-boehmite, gibbsite and aluminum trichloride, or any combination thereof. A convenient source of aluminum is pseudo-boehmite, particularly when producing a silicoaluminophosphate molecular sieve.

Non-limiting examples of phosphorus sources, which may also include aluminum-containing phosphorus compositions, include phosphoric acid, organic phosphates such as triethyl phosphate, and crystalline or amorphous aluminophosphates such as $AlPO_4$, phosphorus salts, or combinations thereof. A convenient source of phosphorus is phosphoric acid, particularly when producing a silicoaluminophosphate.

In general, templating agents or templates include compounds that contain elements of Group 15 of the Periodic Table of Elements, particularly nitrogen, phosphorus, arsenic and antimony. Typical templates also contain at least one alkyl or aryl group, such as an alkyl or aryl group having from 1 to 10 carbon atoms, for example from 1 to 8 carbon atoms. Preferred templates are nitrogen-containing compounds, such as amines, quaternary ammonium compounds and combinations thereof. Suitable quaternary ammonium compounds are represented by the general formula $R_4N^+$, where each R is hydrogen or a hydrocarbyl or substituted hydrocarbyl group, preferably an alkyl group or an aryl group having from 1 to 10 carbon atoms.

Non-limiting examples of templates include tetraalkyl ammonium compounds including salts thereof, such as tetramethyl ammonium compounds, tetraethyl ammonium compounds, tetrapropyl ammonium compounds, and tetrabutylammonium compounds, cyclohexylamine, morpholine, di-n-propylamine (DPA), tripropylamine, triethylamine (TEA), triethanolamine, piperidine, cyclohexylamine, 2-methylpyridine, N,N-dimethylbenzylamine, N,N-diethylethanolamine, dicyclohexylamine, N,N-dimethylethanolamine, choline, N,N'-dimethylpiperazine, 1,4-diazabicyclo(2,2,2) octane, N',N',N,N-tetramethyl-(1,6)hexanediamine, N-methyldiethanolamine, N-methyl-ethanolamine, N-methyl piperidine, 3-methyl-piperidine, N-methylcyclohexylamine, 3-methylpyridine, 4-methyl-pyridine, quinuclidine, N,N'-dimethyl-1,4-diazabicyclo(2,2,2) octane ion; di-n-butylamine, neopentylamine, di-n-pentylamine, isopropylamine, t-butylamine, ethylenediamine, pyrrolidine, and 2-imidazolidone. Preferred templates are selected from the group consisting of tetraethyl ammonium salts, cyclopentylamine, aminomethyl cyclohexane, piperidine, triethylamine, cyclohexylamine, tri-ethyl hydroxyethylamine, morpholine, dipropylamine (DPA), pyridine, isopropylamine, heated degraded forms thereof, and combinations thereof.

The pH of the synthesis mixture containing at a minimum a silicon, aluminum, optionally a phosphorus composition, and a templating agent, is generally in the range of from 2 to 10, such as from 4 to 9, for example from 5 to 8.

Generally, the synthesis mixture described above is sealed in a vessel and heated, preferably under autogenous pressure, to a temperature in the range of from about 80° C. to about 250° C., such as from about 100° C. to about 250° C., for example from about 125° C. to about 225° C., such as from about 150° C. to about 180° C.

In one embodiment, the synthesis of molecular sieve crystalline particles is aided by seeds from another or the same framework type molecular sieve.

The time required to form the crystalline particles is usually dependent on the temperature and can vary from immediately up to several weeks. Typically, the crystallization time is from about 30 minutes to around 2 weeks, such as from about 45 minutes to about 240 hours, for example from about 1 hour to about 120 hours. The hydrothermal crystallization may be carried out with or without agitation or stirring.

One method for crystallization involves subjecting an aqueous reaction mixture containing an excess amount of a templating agent to crystallization under hydrothermal conditions, establishing an equilibrium between molecular sieve formation and dissolution, and then, removing some of the excess templating agent and/or organic base to inhibit dissolution of the molecular sieve. See, for example, U.S. Pat. No. 5,296,208, which is herein fully incorporated by reference.

Other methods for synthesizing molecular sieves or modifying molecular sieves are described in U.S. Pat. No. 5,879,655 (controlling the ratio of the templating agent to phosphorus), U.S. Pat. No. 6,005,155 (use of a modifier without a salt), U.S. Pat. No. 5,475,182 (acid extraction), U.S. Pat. No. 5,962,762 (treatment with transition metal), U.S. Pat. Nos. 5,925,586 and 6,153,552 (phosphorus modified), U.S. Pat. No. 5,925,800 (monolith supported), U.S. Pat. No. 5,932,512 (fluorine treated), U.S. Pat. No. 6,046,373 (electromagnetic wave treated or modified), U.S. Pat. No. 6,051,746 (polynuclear aromatic modifier), U.S. Pat. No. 6,225,254 (heating template), PCT WO 01/36329 published May 25, 2001 (surfactant synthesis), PCT WO 01/25151 published Apr. 12, 2001 (staged acid addition), PCT WO 01/60746 published Aug. 23, 2001 (silicon oil), U.S. Patent Application Publication No. 20020055433 published May 9, 2002 (cooling molecular sieve), U.S. Pat. No. 6,448,197 (metal impregnation including copper), U.S. Pat. No. 6,521,562 (conductive microfilter), and U.S. Patent Application Publication No. 20020115897 published Aug. 22, 2002 (freeze drying the molecular sieve), which are all herein fully incorporated by reference.

Once the crystalline molecular sieve product is formed, usually in a slurry state, it may be recovered by any standard technique well known in the art, for example, by centrifugation or filtration. The recovered crystalline particle product, normally termed the "wet filter cake", may then be washed, such as with water, and then dried, such as in air, before being formulated into a catalyst composition. Alternatively, the wet filter cake may be formulated into a catalyst composition directly, that is without any drying, or after only partial drying.

B. Active Metal Oxides

The catalyst of this invention further comprises at least one active metal oxide of one or more metals. Active metal oxides are those metal oxides, typically different from the binder or matrix materials, that, when used in combination with the metalloaluminophosphate molecular sieve, provide benefits in catalytic conversion processes. In particular, active metal oxides are those metal oxides, different from typical binders and/or matrix materials that, when used in combination with a molecular sieve in a catalyst composition, are effective in extending of the useful life of the catalyst composition. Quantification of the extension in catalyst life is determined by the Lifetime Enhancement Index (LEI) as defined by the following equation:

$$LEI = \frac{\text{Lifetime of Catalyst in Combination with Active Metal Oxide}}{\text{Lifetime of Catalyst}}$$

where the lifetime of the catalyst or catalyst composition, in the same process under the same conditions, is the cumulative amount of feedstock processed per gram of catalyst composition until the conversion of feedstock by the catalyst composition falls below some defined level, for example 10%. An inactive metal oxide will have little to no effect on the lifetime of the catalyst composition, or will shorten the lifetime of the catalyst composition, and will therefore have a LEI less than or equal to 1. Thus active metal oxides of the invention are those metal oxides, different from typical binders and/or matrix materials, that, when used in combination with a molecular sieve, provide a molecular sieve catalyst composition that has a LEI greater than 1. By definition, a molecular sieve catalyst composition that has not been combined with an active metal oxide will have a LEI equal to 1.0.

It is found that, by including an active metal oxide in combination with a molecular sieve, a catalyst composition can be produced having an LEI in the range of from greater than 1 to 2000, such as from about 1.5 to about 1000. Typically catalyst compositions according to the invention exhibit LEI values greater than 1.1, for example in the range of from about 1.2 to 150, and more particularly greater than 1.3, such as greater than 1.5, such as greater than 1.7, such as greater than 2.

Preferred active metal oxides are oxides of one or more metals selected from the group consisting of Group 2 metals, Group 3 metals, Lanthanide and Actinide series metals, and Group 4 metals of the Periodic Table of the Elements.

In one embodiment of the invention, the catalyst of the invention comprises at least one active metal oxide that is an oxide of one or more metals selected from the Group 2 metals of the Periodic Table of the Elements. Preferably, the active metal oxide component of the catalyst comprises at least one active metal oxide that is an oxide of one or more metals selected from the group consisting of magnesium, calcium, strontium and barium. More preferably, the active metal oxide is magnesium oxide, calcium oxide or barium oxide.

In another embodiment, the catalyst of the invention comprises at least one active metal oxide that is an oxide of one or more metals selected from the Group 3 metals of the Periodic Table of the Elements, including the Lanthanides and Actinides. Preferably, the active metal oxide component of the catalyst comprises at least one active metal oxide that is an oxide of one or more metals selected from the group consisting of scandium, yttrium, lanthanum and cerium. More preferably, the active metal oxide is scandium oxide, yttrium oxide, lanthanum oxide or cerium oxide.

In another embodiment, the catalyst of the invention comprises at least one active metal oxide that is an oxide of one or more metals selected from the Group 4 metals of the Periodic Table of the Elements. Preferably, the active metal oxide component of the catalyst comprises at least one active metal oxide that is an oxide of one or more metals selected from the group consisting of zirconium and hafnium. More preferably, the active metal oxide is zirconium oxide.

In a preferred embodiment, the active metal oxide is an active metal oxide of one of the Group 2 metals and one or more of the Group 3 metals. In another preferred embodiment, the active metal oxide is an active metal oxide of one of the Group 4 metals and one or more of the Group 2 or 3 metals.

In one embodiment, the active metal oxide when combined with a molecular sieve in a catalyst composition enhances the lifetime of the catalyst composition in the conversion of a feedstock comprising methanol, preferably into one or more olefin(s).

In particular, the metal oxides useful herein have an uptake of carbon dioxide at 100° C. of at least 0.03 mg/m$^2$ of the metal oxide, such as at least 0.035 mg/m$^2$ of the metal oxide. Although the upper limit on the carbon dioxide uptake of the metal oxide is not critical, in general the metal oxides useful herein will have a carbon dioxide at 100° C. of less than 10 mg/m$^2$ of the metal oxide, such as less than 5 mg/m$^2$ of the metal oxide. Typically, the metal oxides useful herein have a carbon dioxide uptake of 0.04 to 0.2 mg/m$^2$ of the metal oxide.

In order to determine the carbon dioxide uptake of a metal oxide, the following procedure is adopted. A sample of the metal oxide is dehydrated by heating the sample to about 200° C. to 500° C. in flowing air until a constant weight, the "dry weight", is obtained. The temperature of the sample is then reduced to 100° C. and carbon dioxide is passed over the sample, either continuously or in pulses, again until constant weight is obtained. The increase in weight of the sample in terms of mg/mg of the sample based on the dry weight of the sample is the amount of adsorbed carbon dioxide.

Carbon dioxide uptake is preferably measured using a Mettler TGA/SDTA 851 thermogravimetric analysis system under ambient pressure. The metal oxide sample is dehydrated in flowing air to about 500° C. for one hour. The temperature of the sample is then reduced in flowing helium to 100° C. After the sample has equilibrated at the desired adsorption temperature in flowing helium, the sample is subjected to 20 separate pulses (about 12 seconds/pulse) of a gaseous mixture comprising 10-weight % carbon dioxide with the remainder being helium. After each pulse of the adsorbing gas the metal oxide sample is flushed with flowing helium for 3 minutes. The increase in weight of the sample in terms of mg/mg adsorbent based on the adsorbent weight after treatment at 500° C. is the amount of adsorbed carbon dioxide. The surface area of the sample is measured in accordance with the method of Brunauer, Emmett, and Teller (BET) published as ASTM D 3663 to provide the carbon dioxide uptake in terms of mg carbon dioxide/m$^2$ of the metal oxide.

In one embodiment, the active metal oxide(s) has a BET surface area of greater than 10 m$^2$/g, such as greater than 10 m$^2$/g to about 300 m$^2$/g. In another embodiment, the active metal oxide(s) has a BET surface area greater than 20 m$^2$/g, such as from 20 m$^2$/g to 250 m$^2$/g. In yet another embodiment, the active metal oxide(s) has a BET surface area greater than 25 m$^2$/g, such as from 25 m$^2$/g to about 200 m$^2$/g.

The active metal oxide(s) used herein can be prepared using a variety of methods. It is preferable that the active metal oxide is made from an active metal oxide precursor, such as a metal salt, such as a halide, nitrate, sulfate or acetate. Other suitable sources of the metal oxide include compounds that form the metal oxide during calcination, such as oxychlorides and nitrates. Alkoxides are also suitable sources of the Group 4 metal oxide, for example zirconium n-propoxide.

In one embodiment, the metal oxide is hydrothermally treated under conditions that include a temperature of at least 80° C., preferably at least 100° C. The hydrothermal treatment typically takes place in a sealed vessel at greater than atmospheric pressure. However, a preferred mode of treatment involves the use of an open vessel under reflux conditions. Agitation of the hydrated metal oxide in a liquid medium, for example, by the action of refluxing liquid and/or stirring, promotes the effective interaction of the hydrated oxide with the liquid medium. The duration of the contact of the hydrated oxide with the liquid medium is conveniently at least 1 hour, such as at least 8 hours. The liquid medium for this treatment typically has a pH of about 6 or greater, such as 8 or greater. Non-limiting examples of suitable liquid media include water, hydroxide solutions (including hydroxides of $NH_4^+$, $Na^+$, $K^+$, $Mg^{2+}$, and $Ca^{2+}$), carbonate and bicarbonate solutions (including carbonates and bicarbonates of $NH_4^+$, $Na^+$, $K^+$, $Mg^{2+}$, and $Ca^{2+}$), pyridine and its derivatives, and alkyl/hydroxylamines.

In another embodiment, the active metal oxide is prepared, for example, by subjecting a liquid solution, such as an aqueous solution, comprising a source of ions of a Group 2, 3 or 4 metal to conditions sufficient to cause precipitation of a hydrated precursor of the solid oxide material, such as by the addition of a precipitating reagent to the solution. Conveniently, the precipitation is conducted at a pH above 7. For example, the precipitating agent may be a base such as sodium hydroxide or ammonium hydroxide.

When a mixture of a Group 4 metal oxide with a Group 2 and/or 3 metal oxide is to be prepared, a first liquid solution comprising a source of ions of a Group 4 metal can be combined with a second liquid solution comprising a source of ions of a Group 2 and/or Group 3 metal. This combination of two solutions can take place under conditions sufficient to cause co-precipitation of the mixed oxide material as a solid from the liquid medium. Alternatively, the source of ions of the Group 4 metal and the source of ions of the Group 2 and/or Group 3 metal may be combined into a single solution. This solution may then be subjected to conditions sufficient to cause co-precipitation of a hydrated precursor of the solid mixed oxide material, such as by the addition of a precipitating reagent to the solution.

The temperature at which the liquid medium is maintained during the precipitation is generally less than about 200° C., such as in the range of from about 0° C. to about 200° C. A particular range of temperatures for precipitation is from about 20° C. to about 100° C. The resulting gel is preferably then hydrothermally treated at temperatures of at least 80° C., preferably at least 100° C. The hydrothermal treatment typically takes place in a vessel at atmospheric pressure. The gel, in one embodiment, is hydrothermally treated for up to 10 days, such as up to 5 days, for example up to 3 days.

The hydrated precursor to the metal oxide(s) is then recovered, for example by filtration or centrifugation, and washed and dried. The resulting material can then be calcined, such as in an oxidizing atmosphere, at a temperature of at least 400° C., such as at least 500° C., for example from about 600° C. to about 900° C., and particularly from about 650° C. to about 800° C., to form the active metal oxide or active mixed metal oxide. The calcination time is typically up to 48 hours, such as for about 0.5 to 24 hours, for example for about 1.0 to 10 hours. In one embodiment, calcination is carried out at about 700° C. for about 1 to about 3 hours.

In another embodiment, the Group 4 metal oxide and the Group 2 and/or Group 3 metal oxide are made separately and then contacted together to form the mixed metal oxide that is then contacted with the molecular sieve. For example, the Group 4 metal oxide can be contacted with the molecular sieve prior to introducing the Group 2 and/or Group 3 metal oxide or alternatively, the Group 2 and/or Group 3 metal oxide can be contacted with the molecular sieve prior to introducing the Group 4 metal oxide.

Where the catalyst composition comprises a Group 4 metal oxide and a Group 3 metal oxide, the mole ratio of the Group 4 metal oxide to the Group 3 metal oxide may be in the range of from 1000:1 to 1:1, such as from about 500:1 to 2:1, such as from about 100:1 to about 3:1, such as from about 75:1 to about 5:1 based on the total moles of the Group 4 and Group 3 metal oxides. In addition, the catalyst composition can contain from 1 to 25%, such as from 1 to 20%, such as from 1 to 15%, by weight of Group 3 metal based on the total weight of the mixed metal oxide, particularly where the Group 3 metal oxide is a lanthanum or yttrium metal oxide and the Group 4 metal oxide is a zirconium metal oxide.

Where the catalyst composition comprises a Group 4 metal oxide and a Group 2 metal oxide, the mole ratio of the Group 4 metal oxide to the Group 2 metal oxide may be in the range of from 1000:1 to 1:2, such as from about 500:1 to 2:3, such as from about 100:1 to about 1:1, such as from about 50:1 to about 2:1, based on the total moles of the Group 4 and Group 2 metal oxides. In addition, the catalyst composition can contain from 1 to 25%, such as from 1 to 20%, such as from 1 to 15%, by weight of Group 2 metal based on the total weight of the mixed metal oxide, particularly where the Group 2 metal oxide is calcium oxide and the Group 4 metal oxide is a zirconium metal oxide.

In another embodiment, the active metal oxides are made from active metal oxide precursors, such as metal salts, preferably Group 2 or Group 3 metal salt precursors. Other suitable sources of the Group 2 metal oxide include compounds that form these metal oxides during calcination, such as oxychlorides and nitrates. A further suitable source of the Group 2 or Group 3 metal oxides include salts containing the cation of the Group 2 or Group 3 metals, such as halides, nitrates, and acetates. Alkoxides are also sources of the Group 2 or Group 3 metal oxides.

In one method, the active metal oxide is prepared by the thermal decomposition of metal-containing compounds, such as magnesium oxalate and barium oxalate, at high temperatures, such as 600° C., in flowing air. Thus prepared metal oxides usually have low BET surface area, e.g., less than 30 m²/g.

In another method, the active metal oxide is prepared by the hydrolysis of metal-containing compounds followed by dehydration and calcination. For example, MgO is hydroxylated by mixing the oxide with deionized water, forming a white slurry. The slurry is slowly heated to dryness on a heating plate to form white powder. The white powder is further dried in a vacuum oven at 100° C. for at least 4 hrs, such as for 12 hrs. The dried white powder is then calcined in air at a temperature of at least 400° C., such as at least 500° C., and typically at least 550° C. Thus-prepared active metal oxides generally have higher BET surface area (between 30 to 300 m²/g) than that prepared by thermal decomposition of the active metal oxide precursors.

In yet another method, the active metal oxide is prepared by the so-called aerogel method (Koper, O. B., Lagadic, I., Volodin, A. and Klabunde, K. J., Chem. Mater., 1997, 9, 2468–2480). In this method, Mg powder is reacted under nitrogen purge with anhydrous methanol, to form $Mg(OCH_3)_2$ solution in methanol. The resultant $Mg(OCH_3)_2$ solution is added to toluene. Water is then added dropwise to the Mg(OH)$_2$ solution in methanol-toluene under vigorous stirring. The resultant colloidial suspension of Mg(OH)$_2$ is placed in an autoclave, pressurized to 100 psig (690 kpag) with dry nitrogen, and heated slowly to a final pressure of about 1000 psig (6895 kpag). The supercritical solvent is vented to produce a fine white powder of Mg(OH)$_2$. Nanocrystalline MgO is obtained by heating the fine white powder at 400° C. under vacuum. Such prepared active metal oxides have the highest BET surface area, generally greater than 300 m$^2$/g.

Various methods exist for making mixed metal oxides from Group 2 and Group 3 metal oxide precursors, e.g., wet impregnation, incipient wetness and co-precipitation.

In one embodiment, mixed metal oxides are prepared by impregnating a Group 3 metal oxide precursor onto a Group 2 metal oxide. In a typical preparation, a Group 3 metal oxide precursor such as La(acetylacetonate)$_3$ is dissolved in an organic solvent such as toluene. The amount of solvent used is enough to fill the mesoporous and macroporous volume of the Group 2 metal oxide. The Group 3 metal oxide precursor solution is added dropwise to the Group 2 metal oxide. The wet mixture is dried in a vacuum oven for 1 to 12 hours to remove the solvent. The resulting solid mixture is then calcined at a temperature, e.g., 400° C., high enough to decompose the Group 3 metal oxide precursor into an oxide.

In another embodiment, a mixed oxide is prepared by the incipient wetness technique. Typically, a Group 3 metal oxide precursor such as lanthanum acetate is dissolved in deionized water. The solution is added dropwise to a Group 2 metal oxide. The mixture is dried in a vacuum oven at 50° C. for 1 to 12 hours. The dried mixture is broken up and calcined at 550° C. in air for 3 hours.

In yet another embodiment, a mixed metal oxide is prepared by co-precipitation. An aqueous solution comprising Group 2 and Group 3 metal oxide precursors is subject to conditions sufficient to cause precipitation of a hydrated precursor of the solid oxide materials, such as by the addition of sodium hydroxide or ammonium hydroxide. The temperature at which the liquid medium is maintained during the co-precipitation is typically from about 20° C. to about 100° C. The resulting gel is then hydrothermally treated at temperatures between 50 and 100° C. for several days. The hydrothermal treatment typically takes place at greater than atmospheric pressure.

The resulting material is then recovered, for example by filtration or centrifugation, and washed and dried. The resulting material is then calcined at a temperature of greater than 200° C., preferably greater than 300° C., and more preferably greater 400° C., and most preferably greater than 450° C.

In yet another embodiment, it is preferred to utilize two or more active metal oxides, preferably one Group 4 metal oxide and one Group 2 or Group 3 metal oxide. The active metal oxides useful in the invention are combinable in many ways to form the mixed metal oxides. In an embodiment, the metal oxides are mixed together in a slurry or hydrated state or in a substantially dry or dried state, preferably the metal oxides are contacted in a hydrated state.

III. Catalyst Composition

The catalyst composition of the invention includes any one of the molecular sieves previously described and one or more of the active metal oxides described above, optionally with a binder and/or matrix material different from the active metal oxide(s). Typically, the weight ratio of the molecular sieve to the active metal oxide(s) in the catalyst composition is in the range of from 5 weight percent to 800 weight percent, such as from 10 weight percent to 600 weight percent, particularly from 20 weight percent to 500 weight percent, and more particularly from 30 weight percent to 400 weight percent.

There are many different binders that are useful in forming catalyst compositions. Non-limiting examples of binders that are useful alone or in combination include various types of hydrated alumina, silicas, and/or other inorganic oxide sols. One preferred alumina containing sol is aluminum chlorhydrol. The inorganic oxide sol acts like glue binding the synthesized molecular sieves and other materials such as the matrix together, particularly after thermal treatment. Upon heating, the inorganic oxide sol, preferably having a low viscosity, is converted into an inorganic oxide binder component. For example, an alumina sol will convert to an aluminum oxide binder following heat treatment.

Aluminum chlorhydrol, a hydroxylated aluminum based sol containing a chloride counter ion, has the general formula of $Al_mO_n(OH)_oCl_p \cdot x(H_2O)$ wherein m is 1 to 20, n is 1 to 8, o is 5 to 40, p is 2 to 15, and x is 0 to 30. In one embodiment, the binder is $Al_{13}O_4(OH)_{24}Cl_7 \cdot 12(H_2O)$ as is described in G. M. Wolterman, et al., Stud. Surf. Sci. and Catal., 76, pages 105–144 (1993), which is herein incorporated by reference. In another embodiment, one or more binders are combined with one or more other non-limiting examples of alumina materials such as aluminum oxyhydroxide, γ-alumina, boehmite, diaspore, and transitional aluminas such as α-alumina, β-alumina, γ-alumina, δ-alumina, ε-alumina, κ-alumina, and ρ-alumina, aluminum trihydroxide, such as gibbsite, bayerite, nordstrandite, doyelite, and mixtures thereof.

In another embodiment, the binder is an alumina sol, predominantly comprising aluminum oxide, optionally including some silicon. In yet another embodiment, the binder is peptized alumina made by treating an alumina hydrate, such as pseudobohemite, with an acid, preferably an acid that does not contain a halogen, to prepare a sol or aluminum ion solution. Non-limiting examples of commercially available colloidal alumina sols include Nalco 8676 available from Nalco Chemical Co., Naperville, Ill., and Nyacol AL20DW available from Nyacol Nano Technologies, Inc., Ashland, Mass.

Where the catalyst composition contains a matrix material, this is preferably different from the active metal oxide and any binder. Matrix materials are typically effective in reducing overall catalyst cost, acting as thermal sinks to assist in shielding heat from the catalyst composition for example during regeneration, densifying the catalyst composition, and increasing catalyst strength such as crush strength and attrition resistance.

Non-limiting examples of matrix materials include one or more non-active metal oxides including beryllia, quartz, silica or sols, and mixtures thereof, for example silica-magnesia, silica-zirconia, silica-titania, silica-alumina and silica-alumina-thoria. In an embodiment, matrix materials are natural clays such as those from the families of montmorillonite and kaolin. These natural clays include subbentonites and those kaolins known as, for example, Dixie, McNamee, Georgia and Florida clays. Non-limiting examples of other matrix materials include haloysite, kaolinite, dickite, nacrite, or anauxite. The matrix material, such as a clay, may be subjected to well known modification processes such as calcination and/or acid treatment and/or chemical treatment.

In a preferred embodiment, the matrix material is a clay or a clay-type composition, particularly a clay or clay-type composition having a low iron or titania content, and most preferably the matrix material is kaolin. Kaolin has been found to form a pumpable, high solids content slurry, to have a low fresh surface area, and to pack together easily due to its platelet structure. A preferred average particle size of the matrix material, most preferably kaolin, is from about 0.1 µm to about 0.6 µm with a $D_{90}$ particle size distribution of less than about 1 µm.

Where the catalyst composition contains a binder or matrix material, the catalyst composition typically contains from about 1% to about 80%, such as from about 5% to about 60%, and particularly from about 5% to about 50%, by weight of the molecular sieve based on the total weight of the catalyst composition.

Where the catalyst composition contains a binder and a matrix material, the weight ratio of the binder to the matrix material is typically from 1:15 to 1:5, such as from 1:10 to 1:4, and particularly from 1:6 to 1:5. The amount of binder is typically from about 2% by weight to about 30% by weight, such as from about 5% by weight to about 20% by weight, and particularly from about 7% by weight to about 15% by weight, based on the total weight of the binder, the molecular sieve and matrix material. It has been found that a higher sieve content and lower matrix content increases the molecular sieve catalyst composition performance, whereas a lower sieve content and higher matrix content improves the attrition resistance of the composition.

The catalyst composition typically has a density in the range of from 0.5 g/cc to 5 g/cc, such as from 0.6 g/cc to 5 g/cc, for example from 0.7 g/cc to 4 g/cc, particularly in the range of from 0.8 g/cc to 3 g/cc.

IV. Method of Making the Catalyst Composition

In making the catalyst composition, the molecular sieve is first formed and is then physically mixed with the active metal oxide, preferably in a substantially dry, dried, or calcined state. Most preferably the molecular sieve and active metal oxides are physically mixed in their calcined state. Mixing can be achieved by any method known in the art, such as mixing with a mixer muller, drum mixer, ribbon/paddle blender, kneader, or the like.

Where the catalyst composition contains a matrix and/or binder, the molecular sieve is conveniently initially formulated into a catalyst precursor with the matrix and/or binder and the active metal oxide is then combined with the formulated precursor. The active metal oxide can be added as unsupported particles or can be added in combination with a support, such as a binder or matrix material. The resultant catalyst composition can then be formed into useful shaped and sized particles by conventional techniques such as spray drying, pelletizing, extrusion, and the like.

In one embodiment, the molecular sieve composition and the matrix material, optionally with a binder, are combined with a liquid to form a slurry and then mixed, preferably rigorously mixed, to produce a substantially homogeneous mixture containing the molecular sieve composition. Non-limiting examples of suitable liquids include one or a combination of water, alcohol, ketones, aldehydes, and/or esters. The most preferred liquid is water. In one embodiment, the slurry is colloid-milled for a period of time sufficient to produce the desired slurry texture, sub-particle size, and/or sub-particle size distribution.

The molecular sieve composition and matrix material, and the optional binder, can be combined in the same or different liquids, and can be combined in any order, together, simultaneously, sequentially, or a combination thereof. In the preferred embodiment, the same liquid, preferably water is used. The molecular sieve composition, matrix material, and optional binder, are combined in a liquid as solids, substantially dry or in a dried form, or as slurries, together or separately. If solids are added together as dry or substantially dried solids, it is preferable to add a limited and/or controlled amount of liquid.

In one embodiment, the slurry of the molecular sieve composition, binder and matrix materials are mixed or milled to achieve a sufficiently uniform slurry of sub-particles of the molecular sieve catalyst composition that is then fed to a forming unit that produces the molecular sieve catalyst composition. In a preferred embodiment, the forming unit is spray dryer. Typically, the forming unit is maintained at a temperature sufficient to remove most of the liquid from the slurry, and from the resulting molecular sieve catalyst composition. The resulting catalyst composition when formed in this way takes the form of microspheres.

When a spray drier is used as the forming unit, typically, the slurry of the molecular sieve composition and matrix material, and optionally a binder, is co-fed to the spray drying volume with a drying gas with an average inlet temperature ranging from 200° C. to 550° C., and a combined outlet temperature ranging from 100° C. to about 225° C. In an embodiment, the average diameter of the spray dried formed catalyst composition is from about 40 µm to about 300 µm, such as from about 50 µm to about 250 µm, for example from about 50 µm to about 200 µm, and conveniently from about 65 µm to 90 µm.

Other methods for forming a molecular sieve catalyst composition are described in U.S. Pat. No. 6,509,290 (Vaughn et al., spray drying using a recycled molecular sieve catalyst composition), which is incorporated herein by reference.

Once the molecular sieve catalyst composition is formed in a substantially dry or dried state, to further harden and/or activate the formed catalyst composition, a heat treatment such as calcination, at an elevated temperature is usually performed. Typical calcination temperatures are in the range from about 400° C. to about 1,000° C., such as from about 500° C. to about 800° C., such as from about 550° C. to about 700° C. Typical calcination environments are air (which may include a small amount of water vapor), nitrogen, helium, flue gas (combustion product lean in oxygen), or any combination thereof.

In a preferred embodiment, the catalyst composition is heated in nitrogen at a temperature of from about 600° C. to about 700° C. Heating is carried out for a period of time typically from 30 minutes to 15 hours, such as from 1 hour to about 10 hours, for example from about 1 hour to about 5 hours, and particularly from about 2 hours to about 4 hours.

V. Hydrocarbon Pretreatment Composition

The hydrocarbon that is used to pretreat the molecular sieve composition is one that can be adsorbed into the porous framework of the structure of the molecular sieve. Preferably, the hydrocarbon has a kinetic diameter less than the average pore opening of the molecular sieve.

The hydrocarbon is contacted with the molecular sieve so as to form an integrated hydrocarbon co-catalyst within the pore structure of the molecular sieve. The integrated hydrocarbon co-catalyst is preferably a single ring aromatic compound. More preferably, the integrated hydrocarbon co-catalyst is a benzene-based compound. Still more preferably, the integrated hydrocarbon co-catalyst is identified by Solid State Nuclear Magnetic Resonance (SSNMR) spectra comprising a peak in the 18 ppm to 40 ppm region and a peak in the 120 ppm to 150 ppm region. Alternatively, the intensity of the peak in the 18 ppm to 40 ppm region is negligible, with a single peak near 128 ppm. In one embodiment, the molecular sieve exhibits a ratio in the intensity of the peak in the 18 ppm to 40 ppm region to the intensity of the peak in the 120 ppm to 150 ppm region of not greater than about 1.0. More preferably, the molecular sieve exhibits a ratio in the intensity of the peak in the 18 ppm to 40 ppm region to the intensity of the peak in the 120 ppm to 150 ppm region of between about 0.15 and 0.7.

Enough hydrocarbon is used to pretreat fresh or regenerated molecular sieve to form the active co-catalyst. The hydrocarbon pretreatment composition provides a substantial increase in the amount of ethylene and propylene produced in the oxygenate to olefin reaction process. Typically, an effective amount of hydrocarbon as a pretreatment agent will result in an increase of at least 2 wt % ethylene and propylene in the olefin product. Preferably, the amount of hydrocarbon applied as a pretreatment agent will result in an increase of at least 3 wt % ethylene and propylene in the olefin product, more preferably at least 4 wt % ethylene and propylene in the olefin product.

In one embodiment, the hydrocarbon contacting the molecular sieve in the pretreatment zone comprises one or more oxygenated hydrocarbons or olefins having a kinetic diameter less than the average pore opening of the molecular sieve. Preferably, the hydrocarbon contacting the molecular sieve in the pretreatment zone comprises an alcohol, olefin, aldehyde, ketone, ether or any combination thereof.

In a particular embodiment, the hydrocarbon contacting the molecular sieve in the pretreatment zone comprises a $C_1$–$C_4$ alcohol. More preferably, the hydrocarbon contacting the molecular sieve in the pretreatment zone comprises methanol or ethanol.

In another embodiment, the hydrocarbon contacting the molecular sieve in the pretreatment zone comprises a $C_3$–$C_7$ olefin. Preferably, the hydrocarbon contacting the molecular sieve in the pretreatment zone comprises butene, pentene, hexene, or heptene.

In yet another embodiment, the hydrocarbon contacting the molecular sieve in the pretreatment zone comprises a $C_2$–$C_6$ aldehyde. Preferably, the hydrocarbon contacting the molecular sieve in the pretreatment zone comprises acetaldehyde, propionaldehyde, or butyraldehyde.

In another embodiment, the hydrocarbon contacting the molecular sieve in the pretreatment zone comprises a $C_3$–$C_6$ ketone. Preferably, the hydrocarbon contacting the molecular sieve in the pretreatment zone comprises acetone, butanone, or pentanone.

In still another embodiment, the hydrocarbon contacting the molecular sieve in the pretreatment zone comprises a $C_2$–$C_8$ ether. Preferably, the hydrocarbon contacting the molecular sieve in the pretreatment zone comprises dimethyl ether, methyl ethyl ether, diethyl ether, methyl propyl ether, ethyl propyl ether, dipropyl ether, methyl butyl ether, ethyl butyl ether, propyl butyl ether, or dibutyl ether.

VI. Pretreatment Conditions

According to the invention, fresh, regenerated, or a combination of fresh and regenerated molecular sieve is pretreated with the pretreatment composition in a pretreatment zone to form an integrated hydrocarbon co-catalyst within the porous framework of the molecular sieve. Effective pretreatment of the molecular sieve is obtained over a wide range of temperatures, pressures and space velocities.

In general, the temperature in the pretreatment zone is from about 150° C. to about 850° C. Preferably, the temperature in the pretreatment zone is from about 200° C. to about 800° C., more preferably from about 250° C. to about 750° C.

The temperature in the pretreatment zone can be lower, higher, or the same as that in the reaction zone. In a preferred embodiment, the pretreatment temperature (i.e., the temperature in the pretreatment zone) is at least about the same as or greater than the oxygenate reaction temperature (i.e., the temperature in the oxygenate reaction zone). Preferably, the pretreatment temperature is greater than the oxygenate reaction temperature. Desirably, the temperature in the pretreatment zone is at least 10° C. higher than that in the oxygenate reaction zone. Preferably, the temperature in the pretreatment zone is at least 25° C., more preferably at least 50° C., and most preferably at least about 100° C. higher than that in the reaction zone.

In one embodiment, the temperature in the pretreatment zone is at least 450° C. Preferably, the temperature in the pretreatment zone is at least 500° C., and most preferably at least 550° C.

Pretreatment of the molecular sieve is particularly effective on fresh, activated catalyst, or regenerated catalyst. Such catalyst is substantially low in total carbon content. As the fresh or regenerated catalyst contacts the olefin pretreatment composition, the integrated hydrocarbon co-catalyst forms within the internal pore structure of the molecular sieve. In one embodiment, the molecular sieve that contacts the olefin pretreatment composition to form the integrated hydrocarbon co-catalyst has a total carbon content of not greater than about 2 wt % prior to contact with the olefin pretreatment composition. Preferably the molecular sieve catalyst that contacts the olefin pretreatment composition has a total carbon content of not greater than about 1.5 wt %, more preferably not greater than about 1 wt %, and most preferably not greater than about 0.5 wt %, prior to contact with the olefin pretreatment composition.

Following pretreatment, the molecular sieve contains the integrated hydrocarbon co-catalyst, which is a benzene type compound, within the various cages of the internal pore structure. In addition to using SSNMR to determine appropriate pretreatment of the molecular sieve, an additional embodiment involves measuring hydrocarbon content of the molecular sieve that has contacted the olefin pretreatment composition. In one embodiment, the molecular sieve containing the integrated hydrocarbon co-catalyst has a hydrocarbon content of at least 0.1 wt %, preferably at least 1 wt %, more preferably at least about 5 wt %, and most preferably at least about 10 wt %, based on total weight of the molecular sieve, which excludes non-molecular sieve components such as binder, matrix, etc., which are optionally present in a catalyst composition.

The weight hourly space velocity (WHSV), defined as the total weight of the pretreatment stream per hour, excluding any diluents, per weight of molecular sieve in the catalyst composition, typically ranges in the pretreatment zone from about 1 $hr^{-1}$ to about 5000 $hr^{-1}$, such as from about 2 $hr^{-1}$ to about 3000 $hr^{-1}$, for example from about 5 $hr^{-1}$ to about 1500 $hr^{-1}$, and conveniently from about 10 $hr^{-1}$ to about 1000 $hr^{-1}$. In one embodiment, the WHSV in the pretreatment zone is greater than 20 $hr^{-1}$ and, where feedstock contains methanol and/or dimethyl ether, is in the range of from about 20 $hr^{-1}$ to about 300 $hr^{-1}$.

The pretreatment zone can be contained in a separate pretreatment zone or within a reactor vessel where the catalytic conversion of oxygenate to olefin takes place. In one embodiment, a separate pretreatment vessel is used. In a particular embodiment, the pretreatment vessel is an auxiliary fluidized bed reactor associated with the oxygenate conversion reactor and regenerator system. The auxiliary reactor is capable of continuously receiving catalyst from the regenerator and subsequently supplying pretreated catalyst to the oxygenate conversion reactor. Depending on the reactivity of the pre-treatment hydrocarbons, the fluidized bed pretreatment can be operated, optionally, as a dense bed system (in bubbling mode, U<1 ft/s, or in turbulent mode 1<U<3–5 ft/s) or a transport bed system (U>3–5 ft/s).

In another embodiment, pretreatment is carried out within the same vessel where the catalytic conversion of oxygenate to olefin product takes place. Preferably, two separate temperature zones are maintained to get proper introduction of hydrocarbon and formation of the integrated hydrocarbon co-catalyst. In one aspect, the molecular sieve to be pretreated is introduced into one zone along with the olefin pretreatment composition to form the integrated hydrocarbon co-catalyst. Then, the pretreated molecular sieve containing the integrated hydrocarbon co-catalyst is sent to the other zone and contacted with oxygenate to convert the oxygenate to olefin product. Operating conditions in the two zones are controlled for pretreatment and oxygenate reaction conditions. Either zone or both zones optionally includes heating or cooling equipment such as heat exchangers, steam coils, and cooling coils. In one embodiment, the pretreatment zone includes cooling equipment.

VII. Converting Oxygenate to Olefins Using Pretreated Catalysts

One embodiment of the invention is directed to a process of converting a feedstock to one or more olefin(s). Typically, the feedstock contains one or more aliphatic-containing compounds such that the aliphatic moiety contains from 1 to about 50 carbon atoms, such as from 1 to 20 carbon atoms, for example from 1 to 10 carbon atoms, and particularly from 1 to 4 carbon atoms.

Non-limiting examples of aliphatic-containing compounds include alcohols such as methanol and ethanol, alkyl mercaptans such as methyl mercaptan and ethyl mercaptan, alkyl sulfides such as methyl sulfide, alkylamines such as methylamine, alkyl ethers such as dimethyl ether, diethyl ether and methylethyl ether, alkyl halides such as methyl chloride and ethyl chloride, alkyl ketones such as dimethyl ketone, formaldehydes, and various acids such as acetic acid.

In a preferred embodiment of the process of the invention, the feedstock contains one or more oxygenates, more specifically, one or more organic compound(s) containing at least one oxygen atom. In the most preferred embodiment of the process of invention, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts.

Non-limiting examples of oxygenates include methanol, ethanol, n-propanol, isopropanol, methyl ethyl ether, dimethyl ether, diethyl ether, diisopropyl ether, formaldehyde, dimethyl carbonate, dimethyl ketone, acetic acid, and mixtures thereof.

In the most preferred embodiment, the feedstock is selected from one or more of methanol, ethanol, dimethyl ether, diethyl ether or a combination thereof, more preferably methanol and dimethyl ether, and most preferably methanol.

The various feedstocks discussed above, particularly a feedstock containing an oxygenate, more particularly a feedstock containing an alcohol, is converted primarily into one or more olefin(s). The olefin(s) produced from the feedstock typically have from 2 to 30 carbon atoms, preferably 2 to 8 carbon atoms, more preferably 2 to 6 carbon atoms, still more preferably 2 to 4 carbons atoms, and most preferably are ethylene and/or propylene.

The pretreated catalyst composition of the invention is particularly useful in the process that is generally referred to as the gas-to-olefins (GTO) process or, alternatively, the methanol-to-olefins (MTO) process. In this process, an oxygenated feedstock, most preferably a methanol-containing feedstock, is contacted with the pretreated molecular sieve catalyst composition in an oxygenate conversion zone into one or more olefin products, preferably and predominantly olefin products comprised of a majority of ethylene and propylene.

Using the pretreated catalyst composition of the invention for the conversion of a feedstock, preferably a feedstock containing one or more oxygenates, the amount of olefin(s) produced based on the total weight of hydrocarbon produced is greater than 50 weight percent, typically greater than 60 weight percent, such as greater than 70 weight percent, and preferably greater than 75 weight percent. In one embodiment, the amount of ethylene and/or propylene produced based on the total weight of hydrocarbon product produced is greater than 65 weight percent, such as greater than 70 weight percent, for example greater than 75 weight percent, and preferably greater than 78 weight percent. Typically, the amount ethylene produced in weight percent based on the total weight of hydrocarbon product produced, is greater than 30 weight percent, such as greater than 35 weight percent, for example greater than 40 weight percent. In addition, the amount of propylene produced in weight percent based on the total weight of hydrocarbon product produced is greater than 20 weight percent, such as greater than 25 weight percent, for example greater than 30 weight percent, and preferably greater than 35 weight percent.

In addition to the oxygenate component, such as methanol, the feedstock may contains one or more diluent(s), which are generally non-reactive to the feedstock or molecular sieve catalyst composition and are typically used to reduce the concentration of the feedstock. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The diluent, for example water, may be used either in a liquid or a vapor form, or a combination thereof. The diluent may be either added directly to the feedstock entering a reactor or added directly to the reactor, or added with the molecular sieve catalyst composition.

The oxygenate conversion can be conducted over a wide range of temperatures, such as in the range of from about 200° C. to about 1000° C., for example from about 250° C. to about 800° C., including from about 250° C. to about 750° C., conveniently from about 300° C. to about 650° C., typically from about 350° C. to about 600° C. and particularly from about 350° C. to about 550° C.

Similarly, the oxygenate conversion can be conducted over a wide range of pressures including autogenous pressure. Typically the partial pressure of the feedstock exclusive of any diluent therein employed in the process is in the range of from about 0.1 kPaa to about 5 MPaa, such as from about 5 kPaa to about 1 MPaa, and conveniently from about 20 kPaa to about 500 kPaa.

The weight hourly space velocity (WHSV), defined as the total weight of feedstock excluding any diluents per hour per weight of molecular sieve in the catalyst composition, typically ranges in the oxygenate conversion zone from about 1 $hr^{-1}$ to about 5000 $hr^{-1}$, such as from about 2 $hr^{-1}$ to about 3000 $hr^{-1}$, for example from about 5 $hr^{-1}$ to about 1500 $hr^{-1}$, and conveniently from about 10 $hr^{-1}$ to about 1000 $hr^{-1}$. In one embodiment, the WHSV in the oxygenate conversion zone is greater than 20 $hr^{-1}$ and, where feedstock contains methanol and/or dimethyl ether, is in the range of from about 20 $hr^{-1}$ to about 300 $hr^{-1}$.

Where the process is conducted in a fluidized bed as the oxygenate conversion zone, the superficial gas velocity (SGV) of the feedstock including diluent and reaction products within the reactor system, and particularly within a riser reactor(s), is at least 0.1 meter per second (m/sec), such as greater than 0.5 m/sec, such as greater than 1 m/sec, for example greater than 2 m/sec, conveniently greater than 3 m/sec, and typically greater than 4 m/sec. See for example U.S. patent application Ser. No. 09/708,753 filed Nov. 8, 2000, which is herein incorporated by reference.

The oxygenate conversion is conveniently conducted as a fixed bed process, or more typically as a fluidized bed process (including a turbulent bed process), such as a continuous fluidized bed process, and particularly a continuous high velocity fluidized bed process.

A variety of catalytic reactors can be used as the oxygenate conversion zone. Non-limiting examples include hybrid reactors that have a dense bed or fixed bed reaction zones and/or fast fluidized bed reaction zones coupled together, circulating fluidized bed reactors, riser reactors, and the like. Suitable conventional reactor types are described in for example U.S. Pat. Nos. 4,076,796, 6,287,522 (dual riser), and *Fluidization Engineering*, D. Kunii and O. Levenspiel, Robert E. Krieger Publishing Company, New York, N.Y. 1977, which are all herein fully incorporated by reference.

The preferred reactor types are riser reactors generally described in *Riser Reactor, Fluidization and Fluid-Particle Systems*, pages 48 to 59, F. A. Zenz and D. F. Othmo, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In one practical embodiment, the oxygenate conversion is conducted as a fluidized bed process or high velocity fluidized bed process utilizing a reactor system, a regeneration system and a recovery system.

In one embodiment, the oxygenate conversion reactor system conveniently includes a fluid bed reactor system having a first reaction zone within one or more riser reactor(s) and a second reaction zone within at least one disengaging vessel, typically comprising one or more cyclones. In one embodiment, the one or more riser reactor(s) and disengaging vessel are contained within a single reactor vessel. Fresh feedstock, preferably containing one or more oxygenates, optionally with one or more diluent(s), is fed to the one or more riser reactor(s) into which a molecular sieve catalyst composition or coked version thereof is introduced. In one embodiment, prior to being introduced to the riser reactor(s), the molecular sieve catalyst composition or coked version thereof is contacted with a liquid, preferably water or methanol, and/or a gas, for example, an inert gas such as nitrogen.

In an embodiment, the amount of fresh feedstock fed as a liquid and/or a vapor to the oxygenate conversion zone is in the range of from 0.1 weight percent to about 85 weight percent, such as from about 1 weight percent to about 75 weight percent, more typically from about 5 weight percent to about 65 weight percent based on the total weight of the feedstock including any diluent contained therein. The liquid and vapor feedstocks may be the same composition, or may contain varying proportions of the same or different feedstocks with the same or different diluents.

The feedstock entering the oxygenate conversion zone is preferably converted, partially or fully, into a gaseous effluent that enters an optional disengaging vessel along with the catalyst composition. In a preferred embodiment, cyclone(s) are provided within the disengaging vessel to separate the catalyst composition from the gaseous effluent containing one or more olefin(s) within the disengaging vessel. Although cyclones are preferred, gravity effects within the disengaging vessel can also be used to separate the catalyst composition from the gaseous effluent. Other methods for separating the catalyst composition from the gaseous effluent include the use of plates, caps, elbows, and the like.

In one embodiment, the disengaging vessel includes a stripping zone, typically in a lower portion of the disengaging vessel. In the stripping zone the catalyst composition is contacted with a gas, preferably one or a combination of steam, methane, carbon dioxide, carbon monoxide, hydrogen, or an inert gas such as argon, preferably steam, to recover adsorbed hydrocarbons from the coked catalyst composition that is then introduced to a regeneration system.

The catalyst composition is withdrawn from the disengaging vessel and introduced to the regeneration system to remove carbonaceous material or coke that would have been deposited on the catalyst during the conversion of the oxygenate. The regeneration system comprises a regenerator where the coked catalyst is contacted with a regeneration medium, preferably a gas containing oxygen, under conventional regeneration conditions of temperature, pressure and residence time.

Non-limiting examples of suitable regeneration media include one or more of oxygen, $O_3$, $SO_3$, $N_2O$, NO, $NO_2$, $N_2O_5$, air, air diluted with nitrogen or carbon dioxide, oxygen and water (U.S. Pat. No. 6,245,703), carbon monoxide and/or hydrogen. Suitable regeneration conditions are those capable of burning coke from the coked catalyst composition, preferably to a level less than 0.5 weight percent based on the total weight of the coked molecular sieve catalyst composition entering the regeneration system. For example, the regeneration temperature may be in the range of from about 200° C. to about 1500° C., such as from about 300° C. to about 1000° C., for example from about 450° C. to about 750° C., and conveniently from about 550° C. to 700° C. The regeneration pressure may be in the range of from about 15 psia (103 kPaa) to about 500 psia (3448 kPaa), such as from about 20 psia (138 kPaa) to about 250 psia (1724 kPaa), including from about 25 psia (172 kPaa) to about 150 psia (1034 kPaa), and conveniently from about 30 psia (207 kPaa) to about 60 psia (414 kPaa).

The residence time of the catalyst composition in the regenerator may be in the range of from about one minute to several hours, such as from about one minute to 100 minutes, and the volume of oxygen in the regeneration gas may be in the range of from about 0.01 mole percent to about 5 mole percent based on the total volume of the gas.

The burning of coke in the regeneration step is an exothermic reaction, and in an embodiment, the temperature within the regeneration system is controlled by various techniques in the art including feeding a cooled gas to the regenerator vessel, operated either in a batch, continuous, or semi-continuous mode, or a combination thereof. A preferred technique involves withdrawing the regenerated catalyst composition from the regeneration system and passing it through a catalyst cooler to form a cooled regenerated catalyst composition. The catalyst cooler, in an embodiment, is a heat exchanger that is located either internal or external to the regeneration system. Other methods for operating a regeneration system are in disclosed U.S. Pat. No. 6,290,916 (controlling moisture), which is herein fully incorporated by reference.

In one embodiment, the regenerated catalyst composition is withdrawn from the regeneration system, optionally from a catalyst cooler, and is pretreated in the pretreatment zone. In another embodiment, the regenerated catalyst composition is withdrawn from the regeneration system, optionally from a catalyst cooler, is combined with a fresh molecular sieve catalyst composition and pretreated in the pretreatment zone. A carrier, such as an inert gas, feedstock vapor, steam or the like, may be used, semi-continuously or continuously, to facilitate the introduction of the regenerated catalyst composition to the pretreatment zone.

The olefin product is withdrawn from the oxygenate conversion zone and is sent to a recovery system. Any conventional system for separating and purifying olefin(s) from the product stream from the oxygenate conversion zone can be used. Such systems generally comprise one or more or a combination of various separation, fractionation and/or distillation towers, columns, splitters, or trains, reaction systems such as ethylbenzene manufacture (U.S. Pat. No. 5,476,978) and other derivative processes such as aldehydes, ketones and ester manufacture (U.S. Pat. No. 5,675,041), and other associated equipment, for example various condensers, heat exchangers, refrigeration systems or chill trains, compressors, knock-out drums or pots, pumps, and the like.

Non-limiting examples of these towers, columns, splitters or trains used alone or in combination include one or more of a demethanizer, preferably a high temperature demethanizer, a dethanizer, a depropanizer, a wash tower often referred to as a caustic wash tower and/or quench tower, absorbers, adsorbers, membranes, ethylene splitter, propylene splitter and butene splitter.

Various recovery systems useful for recovering olefin products, such as ethylene, propylene and/or butene, are described in U.S. Pat. No. 5,960,643 (secondary rich ethylene stream), U.S. Pat. Nos. 5,019,143, 5,452,581 and 5,082,481 (membrane separations), U.S. Pat. No. 5,672,197 (pressure dependent adsorbents), U.S. Pat. No. 6,069,288 (hydrogen removal), U.S. Pat. No. 5,904,880 (recovered methanol to hydrogen and carbon dioxide in one step), U.S. Pat. No. 5,927,063 (recovered methanol to gas turbine power plant), and U.S. Pat. No. 6,121,504 (direct product quench), U.S. Pat. No. 6,121,503 (high purity olefins without superfractionation), and U.S. Pat. No. 6,293,998 (pressure swing adsorption), which are all herein fully incorporated by reference.

Other recovery systems that include purification systems, for example for the purification of olefin(s), are described in *Kirk-Othmer Encyclopedia of Chemical Technology*, 4th Edition, Volume 9, John Wiley & Sons, 1996, pages 249–271 and 894–899, which is herein incorporated by reference. Purification systems are also described in for example, U.S. Pat. No. 6,271,428 (purification of a diolefin hydrocarbon stream), U.S. Pat. No. 6,293,999 (separating propylene from propane), and U.S. patent application Ser. No. 09/689,363 filed Oct. 20, 2000 (purge stream using hydrating catalyst), which are herein incorporated by reference.

Generally accompanying most recovery systems is the production, generation or accumulation of additional products, by-products and/or contaminants along with the preferred prime products. The preferred prime products, the light olefins, such as ethylene and propylene, are typically purified for use in derivative manufacturing processes such as polymerization processes. Therefore, in the most preferred embodiment of the recovery system, the recovery system also includes a purification system. For example, the light olefin(s) produced particularly in an oxygenate conversion process are passed through a purification system that removes low levels of by-products or contaminants.

Non-limiting examples of contaminants and by-products include generally polar compounds such as water, alcohols, carboxylic acids, ethers, carbon oxides, sulfur compounds such as hydrogen sulfide, carbonyl sulfides and mercaptans, ammonia and other nitrogen compounds, arsine, phosphine and chlorides. Other contaminants or by-products include hydrogen and hydrocarbons such as acetylene, methyl acetylene, propadiene, butadiene and butyne.

Typically, in converting one or more oxygenates to olefin(s) having 2 or 3 carbon atoms, a minor amount hydrocarbons, particularly olefin(s), having 4 or more carbon atoms is also produced. The amount of $C_4+$ hydrocarbons is normally less than 20 weight percent, such as less than 10 weight percent, for example less than 5 weight percent, and particularly less than 2 weight percent, based on the total weight of the effluent gas withdrawn from the process, excluding water. Typically, therefore the recovery system may include one or more reaction systems for converting the $C_4+$ impurities to useful products. Such impurities can then be used as pretreatment agents in the pretreatment zone.

Non-limiting examples of such reaction systems are described in U.S. Pat. No. 5,955,640 (converting a four carbon product into butene-1). U.S. Pat. No. 4,774,375 (isobutane and butene-2 oligomerized to an alkylate gasoline), U.S. Pat. No. 6,049,017 (dimerization of n-butylene), U.S. Pat. Nos. 4,287,369 and 5,763,678 (carbonylation or hydroformulation of higher olefins with carbon dioxide and hydrogen making carbonyl compounds), U.S. Pat. No. 4,542,252 (multistage adiabatic process), U.S. Pat. No. 5,634,354 (olefin-hydrogen recovery), and Cosyns, J. et al., *Process for Upgrading C3, C4 and C5 Olefinic Streams*, Pet. & Coal, Vol. 37, No. 4 (1995) (dimerizing or oligomerizing propylene, butylene and pentylene), which are all fully herein incorporated by reference.

The preferred light olefin(s) produced by any one of the processes described above are high purity prime olefin(s) products that contain a single carbon number olefin in an amount greater than 80 percent, such as greater than 90 weight percent, such as greater than 95 weight percent, for example at least about 99 weight percent, based on the total weight of the olefin.

In one practical embodiment, the process of the invention forms part of an integrated process for producing light olefin(s) from a hydrocarbon feedstock, preferably a gaseous hydrocarbon feedstock, particularly methane and/or ethane. The first step in the process is passing the gaseous feedstock, preferably in combination with a water stream, to a syngas production zone to produce a synthesis gas (syngas) stream, typically comprising carbon dioxide, carbon monoxide and hydrogen. Syngas production is well known, and typical syngas temperatures are in the range of from about 700° C. to about 1200° C. and syngas pressures are in the range of from about 2 MPa to about 100 MPa. Synthesis gas streams are produced from natural gas, petroleum liquids, and carbonaceous materials such as coal, recycled plastic, municipal waste or any other organic material. Preferably synthesis gas stream is produced via steam reforming of natural gas.

The next step in the process involves contacting the synthesis gas stream generally with a heterogeneous catalyst, typically a copper based catalyst, to produce an oxygenate containing stream, often in combination with water. In one embodiment, the contacting step is conducted at temperature in the range of from about 150° C. to about 450° C. and a pressure in the range of from about 5 MPa to about 10 MPa.

This oxygenate containing stream, or crude methanol, typically contains the alcohol product and various other components such as ethers, particularly dimethyl ether, ketones, aldehydes, dissolved gases such as hydrogen methane, carbon oxide and nitrogen, and fuel oil. The oxygenate containing stream, crude methanol, in the preferred embodiment is passed through a well known purification processes, distillation, separation and fractionation, resulting in a purified oxygenate containing stream, for example, commercial Grade A and AA methanol.

The oxygenate containing stream or purified oxygenate containing stream, optionally with one or more diluents, can then be used as a feedstock in a process to produce light olefin(s), such as ethylene and/or propylene. Non-limiting examples of this integrated process are described in EP-B-0 933 345, which is herein fully incorporated by reference.

In another more fully integrated process, that optionally is combined with the integrated processes described above, the olefin(s) produced are directed to, in one embodiment, one or more polymerization processes for producing various polyolefins. (See for example U.S. patent application Ser. No. 09/615,376 filed Jul. 13, 2000, which is herein fully incorporated by reference.)

Polymerization processes include solution, gas phase, slurry phase and a high pressure processes, or a combination thereof. Particularly preferred is a gas phase or a slurry phase polymerization of one or more olefin(s) at least one of which is ethylene or propylene. These polymerization processes utilize a polymerization catalyst that can include any one or a combination of the molecular sieve catalysts discussed above. However, the preferred polymerization catalysts are the Ziegler-Natta, Phillips-type, metallocene, metallocene-type and advanced polymerization catalysts, and mixtures thereof.

In a preferred embodiment, the integrated process comprises a process for polymerizing one or more olefin(s) in the presence of a polymerization catalyst system in a polymerization reactor to produce one or more polymer products, wherein the one or more olefin(s) have been made by converting an alcohol, particularly methanol, using a molecular sieve catalyst composition as described above. The preferred polymerization process is a gas phase polymerization process and at least one of the olefins(s) is either ethylene or propylene, and preferably the polymerization catalyst system is a supported metallocene catalyst system. In this embodiment, the supported metallocene catalyst system comprises a support, a metallocene or metallocene-type compound and an activator, preferably the activator is a non-coordinating anion or alumoxane, or combination thereof, and most preferably the activator is alumoxane.

The polymers produced by the polymerization processes described above include linear low density polyethylene, elastomers, plastomers, high density polyethylene, low density polyethylene, polypropylene and polypropylene copolymers. The propylene based polymers produced by the polymerization processes include atactic polypropylene, isotactic polypropylene, syndiotactic polypropylene, and propylene random, block or impact copolymers.

VII. EXAMPLES OF PRETREATMENT

A. EXAMPLE 1

Fresh SAPO-34 formulated catalyst, 95 mg, was mixed with 1 g of 100-μm silicon-carbide. The mixture was loaded into a microflow reactor made of ¼" silicon-steel tubing. The reactor temperature was brought to 475° C., while the catalyst was under helium flow (46 ml/min), and held for ca. 30 to 40 minutes.

Methanol feed was then introduced into the reactor to contact the fresh, formulated catalyst at a flow rate of 80 μl/min, and a weight hourly space velocity (WHSV) of 100 hr$^{-1}$, with the reactor at a pressure of 25 psig. The effluent product was sampled using a 16-loop Valco valve. Following the methanol conversion reaction, oxygen and helium were flowed across the catalyst to determine the amount of coke deposited on the catalyst.

From 9 to 15 samples of the collected effluent product were analyzed to obtain the weight average selectivity. The samples were analyzed on-line using a Q-column gas chromatograph (Hewlett Packard 6890) equipped with a flame ionization detector. The weight average yields were calculated according to the formula:

$$x_i y_i + (x_2-x_1)(y_1+y_2)/2 + (x_3-x_2)(y_2+y_3)/2 + (x_4-x_3)(y_3+y_4)/2+ \ldots,$$

where $y_i$ and $x_i$ represent yield and g methanol fed/g sieve, respectively. WHSV was reported based on the weight of the sieve. Methanol converted at less than ca. 10% conversion was not included in the calculation. Selectivities were calculated by normalizing the yield data to exclude methanol and dimethyl ether. The results are shown in the Table. $C_1$, $C_2=$, $C_2°$, $C_3=$, $C_3°$, $C_4s$, $C_5+s$, and $C_{2+3}=$ in the Table refer to methane, ethylene, ethane, propene, propane, butenes and butanes, hydrocarbons that contain five or more than five carbons, and ethylene plus propene, respectively.

B. EXAMPLE 2

Example 1 was repeated except that the fresh SAPO-34 catalyst was pretreated with 1-butene prior to contacting with methanol. A total of 1.87 g 1-butene/g sieve was flowed through the reactor to contact the fresh catalyst at 550° C., 25 psig, and 14 hr$^{-1}$ WHSV. After flow of 1-butene across the catalyst in the reactor was stopped, 48 ml/min of helium was flowed through the reactor while reactor temperature was reduced and stabilized at 475° C. for 45 minutes. Methanol was then introduced into the reactor to contact the pretreated catalyst according to the procedure in Example 1. From 9 to 15 samples of the collected effluent product were analyzed as in Example 1. The results are shown in the Table.

C. EXAMPLE 3

Example 2 was repeated, except that the SAPO-34 catalyst contained 20 wt % active metal oxide, based on total weight of the catalyst. The active metal oxide was a mixed metal oxide of $La_2O_3$ and $ZrO_2$, and contained 5 wt % Lanthanum, based on total weight of the active metal oxide. The synthesis of the 5% $La/ZrO_2$ was as follows:

Fifty grams of $ZrOCl_2 \cdot 8H_2O$ were dissolved with stirring in 300 ml of distilled water. Another solution containing 4.2 grams of $La(NO_3)_3 \cdot 6H_2O$ and 300 ml of distill water was prepared. The two solutions were combined with stirring to form a final mixture. The pH of the final mixture, a slurry, was adjusted to approximately 9 by the addition of concentrated ammonium hydroxide (28.9 grams). This slurry was then put in a polypropylene bottle and placed in a steam box (100° C.) for 72 hours. The resulting product formed was recovered by filtration, washed with excess water, and dried overnight at 85° C. A portion of this resulting product was calcined to 700° C. in flowing air for 3 hours to produce an active mixed metal oxide containing a nominal 5 weight percent La based on the final weight of the mixed metal oxide.

The results are shown in the Table.

TABLE

| Ex. No. | $C_1$ | $C_2=$ | $C_2°$ | $C_3=$ | $C_3°$ | $C_4s$ | $C_5 + s$ | Coke | $C_{2+3}=$ | Life (g/g sieve) |
|---|---|---|---|---|---|---|---|---|---|---|
| 1 | 1.75 | 36.50 | 0.26 | 38.57 | 0.58 | 12.70 | 7.21 | 2.42 | 75.07 | 17.08 |
| 2 | 2.56 | 42.70 | 0.29 | 37.53 | 0.25 | 9.37 | 3.88 | 3.42 | 80.24 | 7.07 |
| 3 | 2.71 | 36.26 | 0.25 | 42.00 | 0.28 | 12.71 | 4.65 | 1.13 | 78.26 | 19.62 |

The data in the Table show that pretreating the molecular sieve catalyst results in significantly higher production of ethylene and propylene compared to no pretreatment. The data further show that pretreating a molecular sieve catalyst containing active metal oxide also provides a significantly higher production of ethylene and propylene compared to no pretreatment. Furthermore, the molecular sieve catalyst containing the active metal oxide also shows a significantly increased lifetime compared to the pretreated catalyst containing no active metal oxide.

Having now fully described this invention, it will be appreciated by those skilled in the art that the invention can be performed within a wide range of parameters within what is claimed, without departing from the spirit and scope of the invention.

We claim:

1. A process for making an olefin product from an oxygenate feed, the process comprising the steps of:
   a) providing a catalyst composition, wherein the catalyst comprises a metalloaluminophosphate molecular sieve having a porous framework and an active metal oxide of zirconium oxide and a lanthanum oxide at a mole ratio of the zirconium oxide to the lanthanum oxide from 1000:1 to 1:1;
   b) pretreating the catalyst composition by contacting the catalyst composition with a hydrocarbon in a pretreatment zone to form an integrated hydrocarbon co-catalyst within the porous framework of the molecular sieve; and
   c) contacting the pretreated catalyst composition with an oxygenate in an oxygenate conversion zone to convert the oxygenate to olefin product.

2. The process of claim 1, wherein the active metal oxide has a carbon dioxide uptake at 100° C. of at least 0.035 mg/m$^2$ of the active metal oxide composition.

3. The process of claim 1, wherein the active metal oxide has a carbon dioxide uptake at 100° C. of less than 10 mg/m$^2$ of the active metal oxide.

4. The process of claim 3, wherein the active metal oxide has a carbon dioxide uptake at 100° C. of less than 5 mg/m$^2$ of the active metal oxide.

5. The process of claim 1, wherein the active metal oxide has a surface area of at least 10 m$^2$/g.

6. The process of claim 5, wherein the active metal oxide has a surface area of at least 15 m$^2$/g.

7. The process of claim 1, wherein the metalloaluminophosphate molecular sieve is silicoaluminophosphate molecular sieve.

8. The process of claim 1, wherein the metalloaluminophosphate molecular sieve is comprised of one or a combination of molecular sieves selected from the group consisting of SAPO-5, SAPO-8, SAPO-1, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AlPO-5, AlPO-11, AlPO-18, AlPO-31, AlPO-34, AlPO-36, AlPO-37, AlPO-46, and metal containing molecular sieves thereof.

9. The process of claim 1, wherein the catalyst composition comprises an alumina binder.

10. The process of claim 1, wherein the catalyst composition comprises a clay.

11. The process of claim 1, wherein the hydrocarbon contacting the molecular sieve in the pretreatment zone has a kinetic diameter less than the average pore opening of the molecular sieve.

12. The process of claim 1, wherein the hydrocarbon contacting the molecular sieve in the pretreatment zone comprises an alcohol, olefin, aldehyde, ketone, ether, or any combination thereof.

13. The process of claim 1, wherein the hydrocarbon contacting the molecular sieve in the pretreatment zone comprises methanol, ethanol or any combination thereof.

14. The process of claim 1, wherein the hydrocarbon contacting the molecular sieve in the pretreatment zone comprises butene, pentene, hexene, heptene or any combination thereof.

15. The process of claim 1, wherein the hydrocarbon contacting the molecular sieve in the pretreatment zone comprises acetaldehyde, propionaldehyde, butyraldehyde or any combination thereof.

16. The process of claim 1, wherein the hydrocarbon contacting the molecular sieve in the pretreatment zone comprises acetone, butanone, pentanone or any combination thereof.

17. The process of claim 1, wherein the hydrocarbon contacting the molecular sieve in the pretreatment zone comprises dimethyl ether, methyl ethyl ether, diethyl ether, methyl propyl ether, ethyl propyl ether, dipropyl ether, methyl butyl ether, ethyl butyl ether, propyl butyl ether, dibutyl ether or any combination thereof.

18. The process of claim 1, wherein the pretreatment zone is at a temperature higher than that of the oxygenate conversion zone.

19. The process of claim 1, wherein the pretreatment zone is at a temperature of at least 10° C. higher than that of the oxygenate conversion zone.

20. The process of claim 1, wherein the pretreatment zone is at a temperature of at least 20° C. higher than that of the oxygenate conversion zone.

21. The process of claim 1, wherein the pretreatment zone is at a temperature of at least 50° C. higher than that of the oxygenate conversion zone.

22. The process of claim 1, wherein at least one olefin in the olefin product is contacted with a polyolefin forming catalyst to form polyolefin.

23. A process for making an olefin product from an oxygenate feed, the process comprising the steps of:
   a) providing a catalyst composition, wherein the composition comprises a metalloaluminophosphate molecular sieve having a porous framework, a binder, a matrix material, and an active metal oxide of zirconium oxide and lanthanum oxide at a mole ratio of the zirconium oxide to the lanthanum oxide from 1000:1 to 1:1;
   b) pretreating the catalyst composition by contacting the catalyst composition with a hydrocarbon in a pretreatment zone to form an integrated hydrocarbon co-catalyst within the porous framework of the molecular sieve; and
   c) contacting the pretreated catalyst composition with an oxygenate in an oxygenate conversion zone to convert the oxygenate to olefin product,
   wherein the pretreatment zone is at a temperature the same as or higher than that of the reaction zone.

24. The process of claim 23, wherein the pretreatment zone is at a temperature higher than that of the reaction zone.

25. The process of claim 24, wherein the pretreatment zone is at a temperature of at least 10° C. higher than that of the reaction zone.

26. The process of claim 25, wherein the pretreatment zone is at a temperature of at least 20° C. higher than that of the reaction zone.

27. The process of claim 26, wherein the pretreatment zone is at a temperature of at least 50° C. higher than that of the reaction zone.

28. The process of claim 23, wherein the active metal oxide has a carbon dioxide uptake at 100° C. of at least 0.03 mg/m$^2$ of the active metal oxide composition.

29. The process of claim 28, wherein the active metal oxide has a carbon dioxide uptake at 100° C. of at least 0.035 mg/m$^2$ of the active metal oxide composition.

30. The process of claim 23, wherein the active metal oxide has a carbon dioxide uptake at 100° C. of less than 10 mg/m$^2$ of the active metal oxide.

31. The process of claim 30, wherein the active metal oxide has a carbon dioxide uptake at 100° C. of less than 5 mg/m$^2$ of the active metal oxide.

32. The process of claim 23, wherein the active metal oxide has a surface area of at least 10 m$^2$/g.

33. The process of claim 32, wherein the active metal oxide has a surface area of at least 15 m$^2$/g.

34. The process of claim 23, wherein the metalloaluminophosphate molecular sieve is silicoaluminophosphate molecular sieve.

35. The process of claim 23, wherein the metalloaluminophosphate molecular sieve is comprised of one or a combination of molecular sieves selective from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AlPO-5, AlPO-11, AlPO-18, AlPO-31, AlPO-34, AlPO-36, AlPO-37, AlPO-46, and metal containing molecular sieves thereof.

36. The process of claim 23, wherein the binder comprises an alumina composition.

37. The process of claim 23, wherein the matrix comprises a clay.

38. The process of claim 23, wherein the hydrocarbon contacting the molecular sieve in the pretreatment zone has a kinetic diameter less than the average pore opening of the molecular sieve.

39. The process of claim 23, wherein the hydrocarbon contacting the molecular sieve in the pretreatment zone comprises an alcohol, olefin, aldehyde, ketone, ether or any combination thereof.

40. The process of claim 23, wherein the hydrocarbon contacting the molecular sieve in the pretreatment zone comprises methanol, ethanol or any combination thereof.

41. The process of claim 23, wherein the hydrocarbon contacting the molecular sieve in the pretreatment zone comprises butene, pentene, hexene, heptene or any combination thereof.

42. The process of claim 23, wherein the hydrocarbon contacting the molecular sieve in the pretreatment zone comprises acetaldehyde, propionaldehyde, butyraldehyde or any combination thereof.

43. The process of claim 23, wherein the hydrocarbon contacting the molecular sieve in the pretreatment zone comprises acetone, butanone, pentanone or any combination thereof.

44. The process of claim 23, wherein the hydrocarbon contacting the molecular sieve in the pretreatment zone comprises dimethyl ether, methyl ethyl ether, diethyl ether, methyl propyl ether, ethyl propyl ether, dipropyl ether, methyl butyl ether, ethyl butyl ether, propyl butyl ether, dibutyl ether or any combination thereof.

45. The process of claim 23, wherein at least one olefin in the olefin product is contacted with a polyolefin forming catalyst to form polyolefins.

46. A process for making an olefin product and polyolefin from an oxygenate feed, the process comprising the steps of:
   a) providing a catalyst composition, wherein the catalyst comprises a metalloaluminophosphate molecular sieve having a porous framework and an active metal oxide of zirconium oxide and lanthanum oxide at a mole ratio of the zirconium oxide to the lanthanum oxide from 1000:1 to 1:1;
   b) pretreating the catalyst composition by contacting the molecular sieve in the catalyst composition with a hydrocarbon in a pretreatment zone to form an integrated hydrocarbon co-catalyst within the porous framework of the molecular sieve;
   c) contacting the pretreated catalyst composition with an oxygenate in an oxygenate conversion zone to convert the oxygenate to olefin product; and
   d) contacting at least one olefin in the olefin product with a polyolefin forming catalyst to form polyolefin.

47. The process of claim 46, wherein the active metal oxide has a carbon dioxide uptake at 100° C. of at least 0.03 mg/m$^2$ of the active metal oxide composition.

48. The process of claim 47, wherein the active metal oxide has a carbon dioxide uptake at 100° C. of at least 0.035 mg/m$^2$ of the active metal oxide composition.

49. The process of claim 46, wherein the active metal oxide has a carbon dioxide uptake at 100° C. of less than 10 mg/m$^2$ of the active metal oxide.

50. The process of claim 49, wherein the active metal oxide has a carbon dioxide uptake at 100° C. of less than 5 mg/m$^2$ of the active metal oxide.

51. The process of claim 46, wherein the active metal oxide has a surface area of at least 10 m$^2$/g.

52. The process of claim 51, wherein the active metal oxide has a surface area of at least 15 m$^2$/g.

53. The process of claim 46, wherein the metalloaluminophosphate molecular sieve is silicoaluminophosphate molecular sieve.

54. The process of claim 46, wherein the metalloaluminophosphate molecular sieve is comprised of one or a combination of molecular sieves selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AlPO-5, AlPO-11, AlPO-18, AlPO-31, AlPO-34, AlPO-36, AlPO-37, AlPO-46, and metal containing molecular sieves thereof.

55. The process of claim 46, wherein the catalyst composition comprises an alumina binder.

56. The process of claim 46, wherein the catalyst composition comprises a clay.

57. The process of claim 46, wherein the hydrocarbon contacting the molecular sieve in the pretreatment zone has a kinetic diameter less than the average pore opening of the molecular sieve.

58. The process of claim 46, wherein the hydrocarbon contacting the molecular sieve in the pretreatment zone comprises an alcohol, olefin, aldehyde, ketone, ether, or any combination thereof.

59. The process of claim 46, wherein the hydrocarbon contacting the molecular sieve in the pretreatment zone comprises methanol, ethanol or any combination thereof.

60. The process of claim 46, wherein the hydrocarbon contacting the molecular sieve in the pretreatment zone comprises butene, pentene, hexene, heptene or any combination thereof.

61. The process of claim 46, wherein the hydrocarbon contacting the molecular sieve in the pretreatment zone comprises acetaldehyde, propionaldehyde, butyraldehyde or any combination thereof.

62. The process of claim 46, wherein the hydrocarbon contacting the molecular sieve in the pretreatment zone comprises acetone, butanone, pentanone or any combination thereof.

63. The process of claim 46, wherein the hydrocarbon contacting the molecular sieve in the pretreatment zone comprises dimethyl ether, methyl ethyl ether, diethyl ether, methyl propyl ether, ethyl propyl ether, dipropyl ether, methyl butyl ether, ethyl butyl ether, propyl butyl ether, dibutyl ether or any combination thereof.

64. The process of claim 46, wherein the pretreatment zone is at a temperature higher than that of the oxygenate conversion zone.

65. The process of claim 46, wherein the pretreatment zone is at a temperature of at least 10° C. higher than that of the oxygenate conversion zone.

66. The process of claim 46, wherein the pretreatment zone is at a temperature of at least 20° C. higher than that of the oxygenate conversion zone.

67. The process of claim 46, wherein the pretreatment zone is at a temperature of at least 50° C. higher than that of the oxygenate conversion zone.

* * * * *